United States Patent
Kamb (12)

(10) Patent No.: US 6,579,675 B2
(45) Date of Patent: *Jun. 17, 2003

(54) METHODS FOR IDENTIFYING NUCLEIC ACID SEQUENCES ENCODING AGENTS THAT EFFECT CELLULAR PHENOTYPES

(75) Inventor: Carl Alexander Kamb, Salt Lake City, UT (US)

(73) Assignee: Deltagen Proteomics, Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 17 days.

(21) Appl. No.: 09/320,080

(22) Filed: May 26, 1999

(65) Prior Publication Data

US 2002/0018992 A1 Feb. 14, 2002

Related U.S. Application Data

(63) Continuation of application No. 08/812,994, filed on Mar. 4, 1997, now Pat. No. 5,955,275, which is a continuation-in-part of application No. 08/800,664, filed on Feb. 14, 1997.

(51) Int. Cl.[7] .......................... C12Q 1/68; C12P 19/34; C07H 21/02; C07H 21/04
(52) U.S. Cl. ....................... 435/6; 435/91.1; 435/91.2; 435/320.1; 536/23.1; 536/24.3; 536/24.31; 536/24.32; 536/24.33
(58) Field of Search ........................ 435/6, 91.2, 91.1, 435/320.1; 536/23.1, 24.3, 24.31, 24.32, 24.33

(56) References Cited

U.S. PATENT DOCUMENTS

| | | | |
|---|---|---|---|
| 5,135,854 A | * 8/1992 | MacKay et al. | 435/69.1 |
| 5,217,889 A | 6/1993 | Roninson et al. | 435/172.3 |
| 5,283,173 A | 2/1994 | Fields et al. | 435/6 |
| 5,364,783 A | 11/1994 | Ruley et al. | 435/235.1 |
| 5,401,629 A | 3/1995 | Harpold et al. | |
| 5,491,084 A | 2/1996 | Chalfie et al. | 435/189 |
| 5,569,588 A | 10/1996 | Ashby et al. | 435/6 |
| 5,691,137 A | 11/1997 | Rosbash et al. | 435/6 |
| 5,928,888 A | 7/1999 | Whitney | |
| 5,945,276 A | 8/1999 | Wu et al. | |
| 5,955,275 A | * 9/1999 | Kamb | 435/6 |

FOREIGN PATENT DOCUMENTS

| | | |
|---|---|---|
| WO | WO 93/08701 | 5/1993 |
| WO | WO93/10245 | 5/1993 |
| WO | WO95/16694 | 6/1995 |
| WO | WO95/19988 | 7/1995 |
| WO | WO97/20078 | 6/1997 |
| WO | WO97/27212 | 7/1997 |
| WO | WO97/48820 | 12/1997 |
| WO | WO98/07886 | 2/1998 |

OTHER PUBLICATIONS

Alberts B., Bray D., et al. (Eds.), *Molecular Biology of the Cell*, Chapter 10, Control of Gene Expression, Second Edition, Garland Publishing, Inc., New York and London, (1989), pp. 551–599.

Anderson M.T., Tjioe I.M., Lorincz M.C., Parks D.R., Herzenberg L.A., Nolan G.P., Herzenberg, "Simultaneous Fluorescence–Activated Cell Sorter Analysis of Two Distinct Transcriptional Elements Within a Single Cell Using Engineered Green Fluorescent Proteins,", L.A., *Proc. Natl. Acad. Sci. (USA)* 93: 16, 8508–8511 (1996).

Badia, E., Duchesne, M.J., Pons, M., and Nicolas, J.C., Membrane Targeting of Firefly Luciferase: A New Bioluminescent Reporter Gene, *Analytical Biochemistry* 217, 333–335 (1994).

Bellen H.J., O'Kane C.J., et al., "P–element–mediated Enhancer Detection: A Versatile Method to Study Development in Drosophila," *Genes Dev.* 3: 1288–1300 (1989).

Chalfie M., Tu Y, et al., "Green Fluorescent Protein as a Marker for Gene Expression," *Science* Feb. 11; 263 : 802–805 (1994).

Cormack B.P., Valdivia R.H., and Falkow S., "FACS–Optimized Mutants of the Green Fluorescent Protein (GFP)," *Gene* 173: 33–38 (1996).

Dorsky, David I., et al., "Detection of HIV–1 Infection with a Green Fluorescent Protein Reporter System", Journal of Acquired Immune Deficiency Syndromes and Human Retrovirology, Lippincott–Raven Publishers, Philadelphia, vol. 13, pp. 308–313 (1996).

Duchange N., Ochoa A., et al., Identification of an Enhancer Involved in the Melanoma–specific Expression of the Tumor Antigen Melanotransferrin Gene, *Nucleic Acids Res.* 20: 2853–2859 (1992).

Fuse N., Yasumoto K., et al., Identification of a Melanocyte–Type Promoter of the Microphthalmia–Associated Transcription Factor Gene, *Biochem. Biophys. Res. Commun.* 219: 702–707 (1996).

(List continued on next page.)

*Primary Examiner*—Jeffrey Fredman
(74) *Attorney, Agent, or Firm*—Bingham McCutchen LLP; Michael J. Shuster

(57) ABSTRACT

Methods for identifying nucleic acid sequences that affect a cellular phenotype are disclosed. The method uses a reporter gene whose level of expression correlates with the phenotype in conjunction with a method or device for measuring the level of reporter expression. An expression library is introduced into the cells, and those cells exhibiting changes in reporter expression level are selected. Expression library inserts from the selected cells are isolated, thereby providing a sub-library enriched for sequences that affect the phenotype reflected by the reporter. Further rounds of sub-library introduction and cell selection may be carried out to provide additional enrichment. Sequences identified using this method may be used to ascertain the identity of additional molecules involved in generating the cellular phenotype.

23 Claims, 8 Drawing Sheets

OTHER PUBLICATIONS

Gervaix, Alain, et al., "A New Reporter Cell Line to Monitor HIV Infection and Drug Susceptibility in vitro", Proc. National Academy of Science, vol. 94, pp. 4653–4658 (Apr. 1997).

Hagen D.C., McCaffrey G., Sprague G.F. Jr., "Pheromone Response Elements Are Necessary and Sufficient for Basal and Pheromone–Induced Transcription of the FUS1 Gene of *Saccharomyces cerevisae*," *Mol. Cell Biol.* 11: 6, 2952–61 (1991).

Herskowitz I., "Functional Inactivation of Genes by Dominant Negative Mutations," *Nature* 329: 219–222 (1987).

Kavathes P., Sukhatme V.P., et al., Isolation of the Gene Encoding the Human T–lymphocyte Differentiation Antigen Leu–2 (T8) By Gene Transfer and Cdna Subtraction, *Proc. Natl. Acad. Sci. (USA)* 81: 7688–7692 (1984).

Koh J., Enders G.H., et al., "Tumour–Derived p16 Alleles Encoding Proteins Defective in Cell–Cycle Inhibition," *Nature* 375: 506–510 (1995).

Lewin B, *Genes V*, Chapter 29, Building the Transcription Complex: Promoters, Factors, and RNA Polymerases, Oxford University Press, Oxford, U.K. (1994), pp. 847–877.

Li, Joachim J., and Herskowitz, Ira, "Isolation of ORC6, a Component of the Yeast Origin Recognition Complex by a One–Hybrid System," *Science*, vol. 262, Dec. 17, 1993.

Qin Z., Kruger–Krasagakes S., et al., "Expression of Tumor Necrosis Factor by Different Tumor Cell Lines Results Either in Tumor Suppression or Augmented Metastasis," *Exp. Med.* 178: 355–360.

Serrano M., Hannon G.J., et al., "A New Regulatory Motif in Cell–Cycle Control Causing Specific Inhibition of Cyclin D/CDK4," *Nature* 366, 704–707 (1993).

Shibata K., Muraosa Y., et al., "Identification of a cis–Acting Element that Enhances the Pigment Cell–specific Expression of the Human Tyrosinase Gene," *J. Biol. Chem.* 267:20584–20588 (1992).

Valdivia, Raphael H., and Falkow, Stanley, "Fluorescence–Based Isolation of Bacterial Genes Expressed Within Host Cells," *Science*, vol. 277, Sep. 26, 1997.

Yokoyama K., Yasumoto K., et al., "Cloning of the Human DOPAchrome Tautomerase/Tyrosinase–related Protein 2 Gene and Identification of Two Regulatory Regions Required for its Pigment Cell–specific Expression," *J. Biol. Chem.* 269: 27080–27087 (1994).

Zou, Yimin, Evans, Sylvia, Chen, Ju, Kuo, Hai–Chien, Harvey, Richard P., and Chien, Kenneth R., "CARP, a cardiac ankyrin repeat protein, is downstream in the Nkx2–5 homeobox gene pathway," *Development* 124, 793–804 (1997).

Kam–Leung, M., et al., "Examination of Mammalian Basic Helix–Loop–Helix Transcription Factors Using a Yeast One–Hybrid System," *DNA and Cell Biology*, 15:1, pp. 1–8, (1996).

Luo Ying, et al., "Cloning and Analysis of DNA–Binding Proteins by Yeast One–Hybrid and One–Two–Hybrid Systems," *BioTechniques*, 20:4, pp. 564–568 (Apr. 1996).

Marcus, Sandra L., "Identificationof COUP–TFII as a peroxisome proliferator response element binding factor using genetic selection in yeast: COUP–TFII activates transcription I yeast but anatagonizes PPAR signaling in Mammalian cells," *Molecular and Cellular Endocrinology* 120:31–39 (1996).

Wang, Michael J., et al., "Molecular cloning of the olfactory neuronal transcription factor Olf–1 by genetic selection in yeast," *Nature*, 364:121–126 (Jul. 8, 1993).

Cornwell, Richard D., et al., "Description of the leukocyte function–associated antigen 1 (LFA–1 or CD11a) promoter," Proceedings of the National Academy of Sciences of the United States of America, 90:4221–4225 (May 1993).

Baillie, Rebecca A., et al., "Transient transfection of chick–embryo hepatocytes," J Nutr. Bioechem 4:431–439 (Jul. 1993).

Fieck A., Wyborski D.L., and Short J.M., "Modifications of the *E. Coli* Lac Repressor for Expression in Eukaryotic cells: Effects of Nuclear Signal Sequences on Protein Activity and Nuclear Accumulation," *Nucleic Acids Res.* 20: 1785 (1992).

Hanahan D., "Heritable Formation of Pancreatic β–Cell Tumours in Transgenic Mice Expressing Recombinant Insulin/Simian Virus 40 Oncogenes," *Nature* May 11; 20: 2233–2239 (1985).

Harrison R.W., and Miller J.C., "Functional Identification of Genes Up–and Down–Regulated by Glucocorticoids in AtT–20 Pituitary Cells Using an Enhancer Trap," *Endocrinology* Jul.; 137:2758–2765 (1996).

Kozak M., "Point Mutations Define a Sequence Flanking the AUG Initiator Codon That Modulates Translation by Eukaryotic Ribosomes," *Cell* Jan. 31; 44: 283–292 (1986).

Iida A., Chen S. T., et al., "Inducible Gene Expression by Retrovirus–Mediated Transfer of a Modified Tetracycline–Regulated System," *J. Virol* 70: 6054–6059(1996).

Myers RM, Tilly K, and Maniatis T., "Fine Structure Genetic Analysis of a β–Globin Promoter," *Science* 232: 613–618 (1986).

Ross J., "mRNA Stability in Mammalian Cells," *Microbiol Rev.*: 423–450 (1995).

Simmons D., and Seed B. "Isolation of a cDNA Encoding CD33, a Differentiation Antigen of Myeloid Progenitor Cell," *J Immunol* 141:2797–2800 (1988).

Valdivia, Raphael H. and Falkow, Stanley, "Bacterial Genetics By Flow Cytometry: Rapid Isolation Of *Salmonella typhimurium* Acid–inducible Promoters By Differential Fluorescence Induction," 1996 Blackwell Science Ltd, *Molecular Microbiology*, 22(2), pp. 367–378.

Wasylyk B., Wasylyk C., and Chambon P., "Short and Long Range Activation by the SV 40 Enhancer," *Nucleic Acids Res.* Jul. 25; 12: 5589–5608 (1984).

Wilkinson G.W., and Akrigg A., "Constitutive and Enhanced Expression from the CMB Major IE Promoter in a Defective Adenovirus Vector, " *Nucleic Acids Res.* May 11; 20: 2233–2239 (1992).

* cited by examiner

PROTEIN COMPLEX

SMALL MOLECULE COMPLEX

PERTURBAGEN COMPLEX

METHODS FOR IDENTIFYING NUCLEIC ACID SEQUENCES ENCODING AGENTS THAT EFFECT CELLULAR PHENOTYPES

RELATED U.S. APPLICATION DATA

This application is a Continuation of Ser. No. 08/812,994, filed Mar. 4, 1997 now U.S. Pat. No. 5,955,275 which is a Continuation-in Part of Ser. No. 08/800,664, filed Feb. 14, 1997 ("Methods for identifying, characterizing, and evolving cell-type specific cis regulatory elements," Carl Alexander Kamb, inventor).

FIELD OF THE INVENTION

The present invention comprises a general procedure applicable in virtually any cell type for identification of nucleic acid sequences that perturb specific biochemical pathways within a cell.

BACKGROUND

Genetic methods have played a major role in efforts to understand the molecular basis for biological phenomena. For example, genetic analysis of the fruit fly, *D. melanogastor*, provided the entry point for isolation of numerous genes that regulate the formation of the fly body. These genes in turn served as probes for isolation of mammalian homologs that have been the primary tools in molecular studies of vertebrate development.

A variety of genetic and biochemical studies have proved that virtually any biological process (i.e., cell behaviors and the like) can be broken down into components. This reductionist approach to biological inquiry aims to understand the greater part of life's complexity in the relatively simple chemical terms of molecules and molecular interactions. In the middle part of the twentieth century, several scientists, perhaps most notably George Beadle, showed that metabolism can be understood as a series of enzymes that act sequentially to convert precursor compounds into the final metabolic products. This insight gave rise to the notion of genetic or biochemical pathways that control cellular processes. More complicated cellular behaviors such as differentiation have recently been defined in terms of genetic programs and pathways. Even disease processes can be thought of in such terms. For example, cancer is a disease characterized by loss of cellular growth control. An effective strategy to study cancer involves the elucidation of cellular growth regulation pathways. Many genes involved in growth control have been identified and substantial progress has been made in understanding the genetic/biochemical circuitry of these component genes.

Some organisms are especially tractable in genetic studies. These organisms typically are either unicellular, or have short life cycles, small genomes, and a variety of other useful features. Other organisms, such as humans, are less tractable. For tractable experimental organisms, two basic approaches to mutant isolation are available. The first method, termed screening, involves the sometimes painstaking inspection of thousands of individual organisms or clones of cells. Those that have the appropriate mutant phenotype are separated from the others and permitted to grow in isolation. In this manner, homogeneous populations of mutants can be grown and analyzed. The second approach involves growth of organisms under conditions that favor the survival of variant phenotypes over the wild type phenotype. In the case of microorganisms, the selection conditions often involve nutritional requirements or resistance to drugs.

The classical models for genetic studies include *E. coli, S. cerevisiae, D. melanogastor*, and *M. musculus*. These organisms share certain features that facilitate genetic studies. First, they can be used to screen and/or select for interesting phenotypic variants (mutants). Second, they can be manipulated in such a way that the underlying genes responsible for specific mutant phenotypes can be localized and isolated by molecular cloning methods. These features permit the analysis of genes in cases where detailed biochemical information about the process under study is unavailable. All that is required at the outset is a tractable experimental organism and a phenotype that can be scored or selected.

In certain organisms such as humans which are of great interest, but in which classical genetic methods of selective breeding cannot be applied, it is still possible to use genetic analysis to identify genes. The techniques are somewhat different and involve retrospective phenotypic and genotypic analysis of kindreds that segregate traits of interest. Such kindreds can be used to determine the approximate location of genes that affect the trait of interest. This approach relies heavily on aspects of heredity that involve sexual reproduction, segregation, and recombination. From rough mapping information, the responsible gene(s) can often be isolated (Miki Y., Swensen J., et al., *Science* 266: 66–71 (1994)).

Cultured cells from multicellular organisms, as well as single-celled organisms, offer the great advantage that genetic studies can be performed on the simplest unit of life, the cell. In many microorganisms, genetic methods are suitably advanced so that detailed genetic analysis of a wide variety of phenotypic traits is possible. In other organisms such as humans, however, genetic studies in cultured cells are still very difficult. Though cultured somatic cells have provided the route to identification of several important human genes, somatic cells have traits that seriously limit their utility. They are diploid; hence mutants with a recessive phenotype are rarely observed. They reproduce clonally; hence it is not possible generally to map interesting mutations. They are often heterogeneous; hence, each cell in a supposedly identical population of cells may differ slightly in phenotype from another cell for a variety of genetic and epigenetic reasons. They do not lend themselves to a large variety of selection schemes. Genetic methods that can mitigate against these problems in human cells would be particularly valuable.

Genes regulate some of the most medically and commercially important processes in biology. A long list of human diseases are caused by mutations or malfunctions of specific genes. Cancer may be the most familiar example, as it involves the sequential alteration of proto-oncogenes and tumor suppressor genes as tumors progress through stages of malignancy (Fearon E. R. and Vogelstein B., *Cell* 61: 759–767 (1990)). Methods capable of identifying the underlying genes that regulate important biological processes such as tumor progression would thus be of great value.

For the foregoing reasons, a general method of genetic analysis in cultured cells is needed. The method should be simple, rapid, and permit identification of components of genetic pathways that regulate traits of interest. It should circumvent many of the obstacles that have interfered with genetic analysis in certain cells and organisms. It should not require an understanding of the detailed basis of a particular phenotype, or the mechanisms that underlie specific cellular behaviors. The method should be generally applicable to a great variety of cells, including cells cultured from somatic tissues of multicellular organisms, and it should sidestep certain disadvantages of somatic cell genetics, including the diploid character of most cells, the difficulty of isolating mutant genes once mutations have been induced, and the heterogeneity of many cell populations.

SUMMARY OF THE INVENTION

The present invention is directed to a method of genetic analysis that satisfies the need for a simple, rapid, and general way to identify components of genetic pathways that regulate traits of interest. The method involves the use of three basic tools: (1) a reporter gene that reflects the phenotypic state of a particular cell; (2) a selection device or method that permits rapid quantitative measurement of the expression levels of the reporter molecule on a cell-by-cell basis; and (3) an expression library, preferably of proteins, protein fragments, or peptides ("perturbagens"), that can be introduced into the chosen cell population (host cells). The reporter gene is typically contained in a construct that places it under the control of a specific cis regulatory element whose activity correlates with the trait of interest. This construct is introduced into a population of host cells such that it is stably maintained and expressed. A genetic library constructed in a second expression vector is introduced into the host cells that harbor the reporter gene construct. This second expression library generates perturbagens in the host cells. The host cells are analyzed using a method or device that quantitatively detects reporter expression levels. Cells with reporter gene expression levels that are decreased or increased relative to the expression observed in cells that contain only the stably expressed reporter, without the perturbagens, are selected and their library inserts are isolated.

The reporter serves as a surrogate for the cellular phenotype and thus must be chosen carefully to reflect the relevant phenotypic state as closely as possible. The reporter may be an endogenous gene, preferably encoding a cell surface marker, expressed by cells with the phenotype of interest, or it may be a foreign gene placed under the control of a cell-type-specific or cell-state-specific promoter that is active in the cells under study. The reporter is expressed in the host cells at a level sufficient to permit its rapid and quantitative determination.

Perturbagens are molecules that act in a transdominant mode to interfere with the function of endogenous cellular components. In the present invention, perturbagens are typically proteinacious: proteins, protein fragments, or peptides; though perturbagens may also be nucleic acids. By expressing perturbagens in cells, it is possible to disrupt specific normal interactions, thus generating a "phenocopy" of a mutant phenotype; that is, although no mutations are created by the method, the function of specific cellular constituents is affected as if the genes encoding these proteins were altered by mutation. Perturbagen genetic libraries are introduced into the host cells that harbor the reporter expression construct in such a way that a single type of each perturbagen (or a small number of different perturbagens) is expressed in a host cell.

The selection device or method is used to screen rapidly through millions of cells that harbor the reporter gene construct for variants that express altered levels of the reporter and to sort (or select) those variant cells away from the majority of cells that express normal levels. This selected population that expresses altered levels of the reporter is used in turn to isolate the resident perturbagens by, e.g., PCR (Ausubel F. M., Brent R., et al., *Current Protocols in Molecular Biology,* John Wiley and Sons, New York (1996)). The selection procedure results in enrichment of the initial population of cells harboring the perturbagen library for cells that contain perturbagen fragments that affect reporter gene expression. The sub-library of perturbagen fragments that influence reporter gene expression can be reintroduced into the host cells and the process of screening/selection can be repeated. The whole cycle is repeated as many times as necessary to obtain a relatively pure sub-library of perturbagen-encoding inserts which, when introduced into the host cells, causes altered reporter gene expression. Each of these perturbagen fragments can be isolated and studied individually.

Because the selection occurs at the population level, and further enrichment cycles are simple to perform, the time associated with gene isolation is greatly reduced. In addition, this approach diminishes the chance that a particular perturbagen isolated according to the methods described herein acts idiosyncratically in a minority of host cells. Screens/selections for virtually any phenotype are possible, limited only by the fidelity with which the reporter represents the cell phenotype of interest.

Perturbagen fragments isolated in this manner produce phenocopies; i.e. they generate the equivalent of genetic mutations. Each fragment encodes a perturbagen that affects expression of the reporter. In principle, any component of the genetic pathway that leads to reporter gene expression is vulnerable to perturbagen disruption. For example, the reporter gene may be expressed only in the presence of a specific transcription factor. If the perturbagen sequesters this factor, or acts upstream of the factor to reduce its activity, reporter gene expression will be reduced. The present invention also can be used to generate a perturbagen disruption that causes a phenotypic transformation such that the original cell type is converted into a different cell type in which the reporter gene is not expressed. Such a perturbagen identifies a master switch; a single molecule capable of dictating the phenotype of the cell.

A cloned perturbagen-encoding sequence may rapidly give direct and indirect information about the pathway it affects. If the perturbagen is derived from a gene or gene fragment, it may be related to a previously identified component of the pathway and its sequence may reveal its identity. The target of the perturbagen may be a second component of that pathway, whose identity can be inferred. Alternatively, the target molecule can be identified by techniques known in the art such as the yeast two-hybrid screen (See Fields S. and Song O. -K., U.S. Pat. No. 5,283,173) or by "suppressor" perturbagen methods outlined infra (Jarvik J. and Botstein D., *Proc. Natl. Acad. Sci. (USA)* 72: 2738–2742 (1975)). Thus, a few selection experiments performed on several millions of cells should enable identification of most or all of the components of a particular pathway which are vulnerable to this type of disruption. Finally, if these components are involved in a process of commercial significance, the perturbagen provides a tool to develop valuable reagents either directly, or as a substrate for screening.

These and other features, aspects, and advantages of the present invention will become better understood with regard to the following description, appended claims, and accompanying drawings.

DEFINITIONS

Figure 1A:
FIG. 1: Perturbagen cartoon. Three examples of intermolecular interactions illustrating: first, a complex between two native proteins in the cell; second, a complex between a small molecule inhibitor of the interaction between the native proteins; and third, a complex between a protein fragment perturbagen derived from the native protein that is the normal binding partner of the other. This perturbagen is expected to behave in a manner similar to the small molecule inhibitor. Furthermore, the perturbagen/target complex serves as the basis for a screen to identify small molecule mimics.

The terms "genetic library" or "library" are interchangeably used to refer to a collection of nucleic acid fragments that may individually range in size from about a few base pairs to about a million base pairs. These fragments are contained as inserts in vectors capable of propagating in certain host cells such as bacterial, fungal, plant, insect, or mammalian cells.

The term "sub-library" refers to a portion of a genetic library that has been isolated by application of a specific screening or selection procedure.

The term "coverage" in the context of a genetic library refers to the level of redundancy of the library. This redundancy is in turn related to the probability that a specific sequence within the nucleic acid sequences that the library is intended to represent is actually present. Coverage is the ratio of the number of library inserts multiplied by the average insert size to the total complexity of the nucleic acid sequences that the library represents.

The term "vector" refers to a nucleic acid sequence that is capable of propagating in particular host cells and can accommodate inserts of foreign nucleic acid. Typically, vectors can be manipulated in vitro to insert foreign nucleic acids and the vectors can be introduced into host cells such that the inserted nucleic acid is transiently or stably present in the host cells.

The term "expression vector" refers to a vector designed to express inserted nucleic acid sequences. Such vectors may contain a powerful promoter located upstream of the insertion site.

The term "expression" in the context of nucleic acids refers to transcription and/or translation of nucleic acids into mRNA and/or protein products.

The term "expression library" refers to a library of nucleic acid fragments contained as inserts in an expression vector.

The term "stable expression" refers to the continued presence and expression of a nucleic acid sequence in a host cell for a period of time that is at least as long as that required to carry out the methods of the present invention. Stable expression can be achieved through integration of the construct into a host cell chromosome, or engineering the construct so that it possesses elements that ensure its continued replication and segregation within the host (i. e., an artificial chromosome), or alternatively, the construct may contain a selectable marker (e.g., a drug resistance gene) so that stable expression of the construct is ensured by growing the host cells under selective conditions (e.g., in drug-containing media).

The term "collection of nucleic acid fragments" refers to a set of nucleic acid molecules from any source. For example, a collection of nucleic acid fragments may comprise total genomic DNA, genomic DNA from one or more chromosomes, cDNA that has been reverse-transcribed from total cellular RNA or from messenger RNA (mRNA), total cellular RNA, mRNA, or a set of nucleic acid molecules synthesized in vitro either individually, or using combinatorial methods. Unless otherwise limited, the term encompasses nucleic acid molecules comprising known analogs of natural nucleotides that can function in a similar manner as naturally occurring nucleotides.

The term "insert" in the context of a library refers to an individual DNA fragment that constitutes a single member of the library.

The term "host cell" refers to a cell of prokaryotic, archaebacterial, or eukaryotic origin that can serve as a recipient for a vector that is introduced by any one of several procedures. The host cell often allows replication and segregation of the vector that resides within. In certain cases, however, replication and/or segregation are irrelevant; expression of vector or insert DNA is the objective. Typical bacterial host cells include *E. coli* and *B. subtilis;* archaebacterial host cells include *S. acidocaldarius* and *H. salinarium;* fungal host cells include *S. cerevisiae* and *S. pombe;* plant cells include those isolated from *A. thaliana,* and *Z maize;* insect host cells include those isolated from *D. melanogastor, A. aegypti,* and *S. frugiperda;* and mammalian cells include those isolated from human tissues and cancers including melanocyte (melanoma), colon (carcinoma), prostate (carcinoma), and brain (glioma, neuroblastoma, astrocytoma).

The term "reporter gene" refers to nucleic acid sequences for which screens or selections can be devised. Reporter genes may encode proteins ("reporters") capable of emitting light such as GFP (Chalfie M., Tu Y, et al., *Science* Feb. 11; 263 :802–805 (1994)), or luciferase (Gould S. J., and Subramani S., *Anal. Biochem.* Nov. 15; 175: 5–13 (1988)), or genes that encode intracellular or cell surface proteins detectable by antibodies such as CD20 (Koh J., Enders G. H., et al., *Nature* 375: 506–510 (1995)). Preferably, the reporters allow the activity of cis regulatory sequences to be monitored in a quantitative manner. Alternatively, reporter genes can confer antibiotic resistance such as hygromycin or neomycin resistance (Santerre R. F., et al., *Gene* 30: 147–156 (1984)).

The terms "bright" and "dim" in the context of a cell sorter refer to the intensity levels of fluorescence (or other modes of light emission) exhibited by particular cells. Bright cells have high intensity emission relative to the bulk population of cells, and by inference, high levels of reporter gene expression; dim cells have low intensity emission relative to the bulk population.

The term "genetic pathway" refers to a set of proteins (or the genes that encode them) that act in concert, or sequentially, to accomplish a specific biochemical function or cellular behavior.

The terms "cis regulatory sequence," "cis sequence," "regulatory sequence," or "regulatory element" are interchangeably used to refer to a nucleic acid sequence that affects the expression of itself or other sequences physically linked on the same nucleic acid molecule. Such sequences may alter gene expression by affecting such things as transcription, translation, or RNA stability. Examples of cis regulatory sequences include promoters, enhancers, or negative regulatory sequences (Alberts B., Bray D., et al. (Eds.), *Molecular Biology of the Cell,* Second Edition, Garland Publishing, Inc., New York and London, (1989); Lewin B, *Gene V,* Oxford University Press, Oxford, U.K. (1994)).

The term "perturbagen" refers to an agent that acts in a transdominant mode to interfere with specific biochemical processes in cells. In the context of the present invention, perturbagens are typically either proteins, protein fragments, or peptides, although the term also encompasses nucleic acids and other organic molecules with similar properties.

The term "transdominant" describes a type of interaction whereby the agent (most typically a perturbagen) is a diffusable substance that can bind its target in solution. Thus, a transdominant agent is dominant as opposed to recessive in a genetic sense, because, e.g., it acts on gene products and not on alleles of genes. The effects of a perturbagen are visible in the presence of wild type alleles of its target.

The term "phenocopy" refers to a phenotypic state or appearance that mimics or resembles the state induced by mutation of a specific gene or genes. This state may, for example, be induced by expression of perturbagens within a particular host cell.

The term "target" in the context of a perturbagen refers to the molecule in the cell (typically a protein) to which the perturbagen binds to exert its effect on cellular phenotype.

The term "flow sorter" refers to a machine that analyzes light emission intensity from cells or other objects and separates these cells or objects according to parameters such as light emission intensity.

DETAILED DESCRIPTION OF PREFERRED EMBODIMENTS

Overview

The present invention comprises methods to identify components of genetic pathways in cultured cells from plants and animals, or unicellular organisms such as yeast, bacteria, and fungi. Three basic tools are involved: (1) a reporter gene under the control of a specific cis regulatory element that reflects the phenotypic state of a particular cell; (2) a selection device or method that permits rapid quantitative measurement of the expression levels of the reporter molecule on a cell-by-cell basis; and (3) an expression library of proteins, protein fragments, or peptides ("perturbagens") that can be introduced into the chosen cell population. Sequences are isolated from the expression library based on their ability to alter the activity of the cis regulatory sequence, as read out by the reporter expression level. The method thus comprises a set of tools and techniques that together permit the identification of components of genetic pathways using a pseudo-genetic approach. The method of the invention can be used in human cells, but it can also be modified easily for use in other mammalian cells, in plant cells, in arthropod cells, and in fungi, archaebacteria and bacteria.

Reporter Genes

Numerous reporter genes have been appropriated for use in expression monitoring and in promoter/enhancer trapping. A reporter comprises any gene product for which screens or selections can be applied. Reporter genes used in the art include the LacZ gene from *E. coli* (Shapiro S. K., Chou J., et al., *Gene* Nov.; 25: 71–82 (1983)), the CAT gene from bacteria (Thiel G., Petersohn D., and Schoch S., *Gene* Feb. 12; 168: 173–176 (1996)), the luciferase gene from firefly (Gould S. J., and Subramani S., 1988), and the GFP gene from jellyfish (Chalfie M. and Prashner D. C., U.S. Pat. No. 5,491,084). This set has been primarily used to monitor expression of genes in the cytoplasm. A different family of genes has been used to monitor expression at the cell surface, e.g., the gene for lymphocyte antigen CD20. Normally a labeled antibody is used that binds to the cell surface marker (e.g., CD20) to quantify the level of reporter (Koh J., Enders G. H., et al., 1995).

Of these reporters, autofluorescent proteins (e.g., GFP) and the cell surface reporters are potentially of greatest use in monitoring living cells, because they act as "vital dyes." Their expression can be evaluated in living cells, and the cells can be recovered intact for subsequent analysis. Vital dyes, however, are not specifically required by the methods of the present invention. It is also very useful to employ reporters whose expression can be quantified rapidly and with high sensitivity. Thus, fluorescent reporters (or reporters that can be labeled directly or indirectly with a fluorophore) are especially preferred. This trait permits high throughput screening on a flow sorter machine such as a fluorescence activated cell sorter (FACS).

GFP is a member of a family of naturally occurring fluorescent proteins, whose fluorescence is primarily in the green region of the spectrum. GFP has been developed extensively for use as a reporter and several mutant forms of the protein have been characterized that have altered spectral properties (Cormack B. P., Valdivia R. H., and Falkow S., *Gene* 173: 33–38 (1996)). High levels of GFP expression have been obtained in cells ranging from yeast to human cells. It is a robust, all-purpose reporter, whose expression in the cytoplasm can be measured quantitatively using a flow sorter instrument such as a FACS.

Genetic Libraries

Genetic libraries typically involve a collection of DNA fragments, usually genomic DNA or cDNA, but sometimes synthetic DNA or RNA, that together represent all or some portion of a genome, a population of mRNAs, or some other set of nucleic acids that contain sequences of interest. Typically, genetic libraries represent sequences in a form that can be manipulated. A total genomic DNA library in principle includes all the sequences present in the genome of an organism propagated as a collection of cloned sequences. It is often desirable to generate a library that is as representative of the input population of nucleic acids as possible. For example, sequences that are present at one to one ratios in the input population (e.g., genome) are present in the library in the same proportion. To achieve reasonable (e.g., >99% predicted) representation of the nucleic acid sequences that the library is intended to contain, a library should have at least 5-fold coverage; that is, the library should contain at least 5-fold excess of total inserts beyond the total number required theoretically to cover the collection of nucleic acid sequences one time. For example, if the library is intended to represent the genome of an organism, the coverage, i.e., the total number of inserts multiplied by the mean insert size divided by the genome complexity, must be at least five. Typically libraries are propagated in vectors that grow in bacterial cells, although eukaryotic cells such as yeast and even human cells can also serve as hosts.

The mean insert size of a library is a variable that can be manipulated within rather broad limits that depend on vector and cell types, among other things. For example, some vectors such as bacterial plasmids accommodate small inserts ranging from a few nucleotides to a few kilobase pairs, whereas others such as yeast artificial chromosomes can accommodate insert sizes that exceed 1,000 kilobase pairs.

The present invention preferably uses genetic libraries that contain inserts on the smaller end of the spectrum. These inserts would most typically be derived from genomes or transcripts of particular organisms, or from synthetic DNA, and would range from, e.g., 10 base pairs to 10 kilobase pairs. The libraries most typically would have coverage that, if possible, exceeded five-fold. The details of library construction, manipulation, and maintenance are known in the art (Ausubel F., Brent R., et al., 1996; Sambrook J., Fritsch E. F., and Maniatis, T., *Molecular Cloning: A Laboratory Manual*, Second Edition, CHSL Press, New York (1989)). In one embodiment of the invention, a library is created according to the following procedure using methods that are well-known in the art. Double stranded cDNA is prepared from random primed mRNA isolated from a particular cell type or tissue. These fragments are treated with enzymes to repair their ends and are ligated into the expression vector described infra. The ligated material is introduced into *E. coli* and clones are selected. A number of individual clones sufficient to achieve reasonable coverage of the mRNA population (e.g., one million clones) is collected, and grown in mass culture for isolation of the resident vectors and their inserts. This process allows large quantities of the library DNA to be obtained in preparation for subsequent procedures described infra.

In specific embodiments of the invention, it is preferable to use non-natural nucleic acid as the starting material for the library. For example, it may be desirable to use a population of synthetic oligonucleotides, e.g., representing all possible sequences of length N, or a subset of all possible sequences, as the input nucleic acid for the library. In addition, it may be desirable to use mixtures of natural and non-natural nucleic acids for library inserts.

Nucleic Acid Transfer

During the last two decades several basic methods have evolved for transferring exogenous nucleic acid into cultured host cells. These methods are well-known in the art (Ausubel F., Brent R.; et al., 1996; Sambrook J., et al., 1989). Some methods give rise primarily to transient expression in host cells; i.e., the expression is gradually lost from the cell population. Other methods can also generate cells that stably express the transferred nucleic acid, though the percentage of stable expressers is typically lower than transient expressers. Such methods include viral and non-viral mechanisms for nucleic acid transfer. In the case of viral transfer, a viral vector is used to carry nucleic acid inserts into the host cell. Depending on the specific virus type, the introduced nucleic acid may remain as an extrachromosomal element (e.g., adenoviruses, Amalfitano A., Begy C. R., and Chamberlain J. S., *Proc. Natl. Acad. Sci.* (*USA*) 93: 3352–3356 (1996)) or may be incorporated into a host chromosome (e.g., retroviruses, Iida A., Chen S. T., et al., *J Virol.* 70: 6054–6059 (1996)).

In the case of non-viral nucleic acid transfer, many methods are available (Ausubel F., Brent R., et al., 1996). One technique for nucleic acid transfer is $CaPO_4$ coprecipitation of nucleic acid. This method relies on the ability of nucleic acid to coprecipitate with calcium and phosphate ions into a relatively insoluble $CaPO_4$ grit, which settles onto the surface of adherent cells on the culture dish bottom. The precipitate is, for reasons that are not clearly understood, absorbed by some cells and the coprecipitated nucleic acid is liberated inside the cell and expressed. A second class of methods employs lipophilic cations that are able to bind DNA by charge interactions while forming lipid micelles. These micelles can fuse with cell membranes, dumping their DNA cargo into the host cell where it is expressed. A third method of nucleic acid transfer is electroporation, a technique that involves discharge of voltage from the plates of a capacitor through a buffer containing DNA and host cells. This process disturbs the bilayer sufficiently that DNA contained in the bathing solution is able to penetrate the cell membrane. A fourth method involves cationic polymers such as DEAE dextran which mediate DNA entry and expression in cultured cells. A fifth method employs ballistic delivery of DNA contained in ice crystals or adsorbed to the surface of miniature projectiles that are shot into cells. Finally, microinjection of DNA can be used, though it is typically quite slow and labor intensive.

Several of these methods often result in the transfer of multiple DNA fragments into individual cells. It is often difficult to limit the quantity of DNA taken up by a single cell to one fragment. However, methods are known in the art to minimize transfer of multiple fragments. For example, by using "carrier" nucleic acid (e.g., DNA such as herring sperm DNA that contains no sequences relevant to the experiment), or reducing the total amount of DNA applied to the host cells, the problem of multiple fragment entry can be reduced. In addition, the invention does not specifically require that each recipient cell have a single type of library sequence. Multiple passages of the library through the host cells (see below), permit sequences of interest to be separated ultimately from sequences that may be present initially as bystanders. Alternatively, it may be useful to take advantage of the feature that many methods of gene transfer into somatic cells deliver multiple copies. This trait may permit more library sequences to be screened in a smaller number of cells, especially since perturbagens act in a transdominant mode; i.e. if a particular cell contains several different perturbagens, one of which alters expression of the reporter, this cell should be collected during screening and the active perturbagen should be recovered (along with others which have no effect).

If it is desirable to carry out genetic experiments on bacterial or fungal cells, a variety of techniques are also available for gene transfer. Electroporation is a particularly flexible method for nucleic acid delivery applicable to most cell types including prokaryotes, fungi, plant and animal cells. In addition, certain mixtures of specific salts can be used with some cells to facilitate DNA entry. For example, $CaCl_2$ works well with *E. coli* and LiOAc works well with *S. cerevisiae*.

Perturbagens

One of the great shortcomings of somatic cell genetics involves the difficulty with which recessive mutations can be observed. The problem can be formulated in statistical terms. If mutations occur in one allele at a frequency of, e.g., one in one million, then the chance that two independent mutations will occur, one in each allele, is the product: one in a trillion. Thus, dominant or codominant mutations are much more readily observed in general. Because of the recessive nature of the vast majority of mutations, somatic cell genetics is limited largely to study of dominant alterations such as overexpression.

Figure 1B:
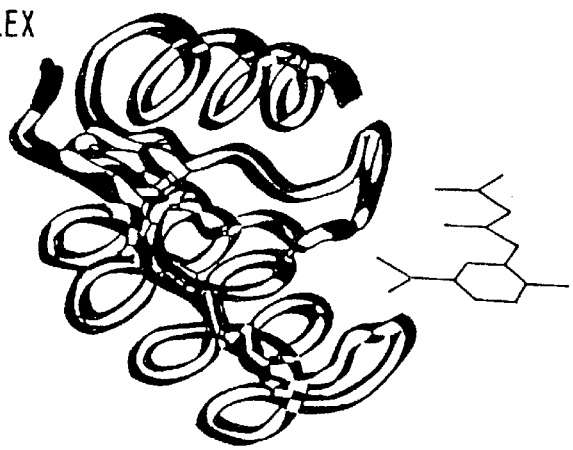
Figure 1C:
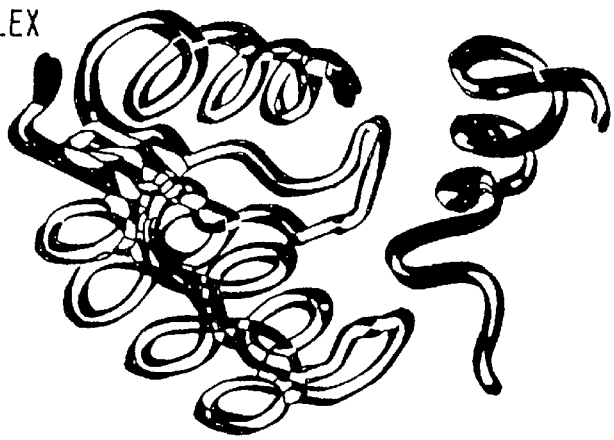

Perturbagens typically are proteins, protein fragments, or peptides (though they may be nucleic acids) that bind other proteins in the cell and thereby disrupt specific biochemical pathways (see FIG. 1). Nature generates perturbagen-like molecules by chance in the case of a certain class of dominant, gain-of-function mutations and in specific cases dominant negative mutant genes have been designed (Herskowitz I., *Nature* 329: 219–222 (1987)). In the present invention, this mode of biochemical/genetic disruption is harnessed and applied in a directed fashion to identify and recover important genes.

Perturbagens can be constructed in a variety of ways. They may be generated from randomly-primed, size-selected cDNA, sheared or digested genomic DNA, synthetic DNA or other sources of nucleic acid. They may be expressed in cells without any additional protein sequences joined to them. Alternatively, they may be fused to other proteins, e.g., GFP or yeast GAL4, by standard methods of molecular cloning (Ausubel et al., 1996). In addition, they may be presented as insertion sequences within specific proteins.

Perturbagen libraries can be constructed using techniques similar to construction of conventional gene and expression libraries as described supra. Such libraries, when introduced into cells with standard vectors such as viruses or by other means, act in a manner analogous to mutagens; that is, the perturbagens induce a phenocopy state in the host cells which mimics the mutant state, but does not directly involve alterations to host cell DNA sequences. The value of perturbagens is based on the ease with which they can be generated and screened, and the readiness with which the perturbagen sequences can be recovered and used to identify elements in the genetic pathways of interest. Furthermore, they act in a mode similar to small molecule therapeutics. Indeed, they are simply the protein equivalent of a small molecule, and they can be used in combination with their targets (binding partners) to screen for small molecule mimics that affect cells in a manner similar to the original protein perturbagen.

In the present invention, perturbagen expression libraries comprised of, e.g., fragmented genomic DNA, random-primed cDNA, or synthetic DNA of random sequence are introduced into host cells engineered to contain a reporter gene under the control of a cell-type-specific cis regulatory sequence. Alternatively, a natural reporter consisting of a membrane protein (or intracellular protein) for which good specific antibodies are available may be used, provided the expression of this protein correlates with a phenotype of interest.

Cells harboring perturbagens are screened by a rapid and quantitative method or device, such as a flow sorter, e.g., a FACS, to identify the population of cells that have altered expression of the reporter. These are collected for analysis as described infra.

Cis Regulatory Elements

In order to drive perturbagen expression in host cells of a particular type, a generic promoter capable of conferring robust, high or moderately high expression is required. These promoters are typically derived from housekeeping genes that are expressed at reasonably high levels in most or all cell types in the organism, or from viruses. Numerous such cis regulatory sequences are known in the art, suitable for driving expression in mammalian cells, insect cells, plant cells, fungi or bacteria (Ausubel et al., 1996; vector database located at: http://www.atcg.com/vectordb/). For example, in eukaryotes the promoter for beta actin is useful (Qin Z., Kruger-Krasagakes S., et al., *J Exp. Med.* 178: 355–360); in plants the Cauliflower Mosaic Virus 35S promoter (Goddijn O. J., Pennings E. J., et al., *Transgenic Res.* 4: 315–323 (1995)); and in general, a promoter that drives high level expression of, e.g., a housekeeping or viral gene can be identified with relative ease using current molecular genetic methods.

To identify cis regulatory sequences that drive reporter gene expression, it is necessary to choose or select sequences that have the appropriate characteristics; that is, because the reporter is intended to act as a surrogate for the phenotypic trait(s) under study, it must be regulated in a manner that approximates the phenotype as closely as possible. Many such sequences are known in the art as tissue-specific regulatory elements (Lewin B., (1994)). Alternatively, such regulatory sequences can be identified by standard procedures that involve: first, isolation of cell- or tissue-specific genes using procedures of differential display, subtractive hybridization, representative difference analysis, and others (Ausubel et al., 1996; and see for discussion: Kamb A., Feldhaus M. J., "Method for the comparative assessment of relative amounts of nucleic acids," U.S.

Patent Application Attorney Docket No. 8835-0005-999); second, the cis regulatory elements that are responsible for the pattern of gene expression can be elucidated by application of standard methods of promoter/enhancer analysis including generation of deletion and linker scanned mutants, and expression assays in cells (Lewin B., 1994; Latchman D. S., *Eukaryotic Transcription Factors,* Second Edition, Academic Press, London (1996); McKnight S. L. and Yamamoto K. R., *Transcriptional Regulation,* CHSL Press, New York (1992)). In addition, genetic methods that fall under the general name of enhancer/promoter traps can be employed to find cis sequences with particular characteristics (see discussion in Ruley and von Melchner, U.S. Pat. No. 5,364,783; Bellen H. J., O'Kane C. J., et al., *Genes Dev.* 3: 1288–1300 (1989)).

Finally, methods for genetic selections of regulatory sequences that have predetermined characteristics as described in the co-pending United States patent application of Kamb C. A. titled, "Methods for identifying, characterizing, and evolving cell-type specific cis regulatory elements", may also be applied to identify useful cis sequences for driving reporter gene expression. The goal is to choose a cis regulatory sequence that is active under the conditions of interest, either by genetic methods, biochemical methods, or by reference to known genes that have the desired expression characteristics. For example, if one desires to study the process of pathogenesis in a particular pathogenic organism, it may be useful to commandeer a promoter that is only active in cells competent for pathogenic invasion of the host.

Expression Vectors

Figure 2:
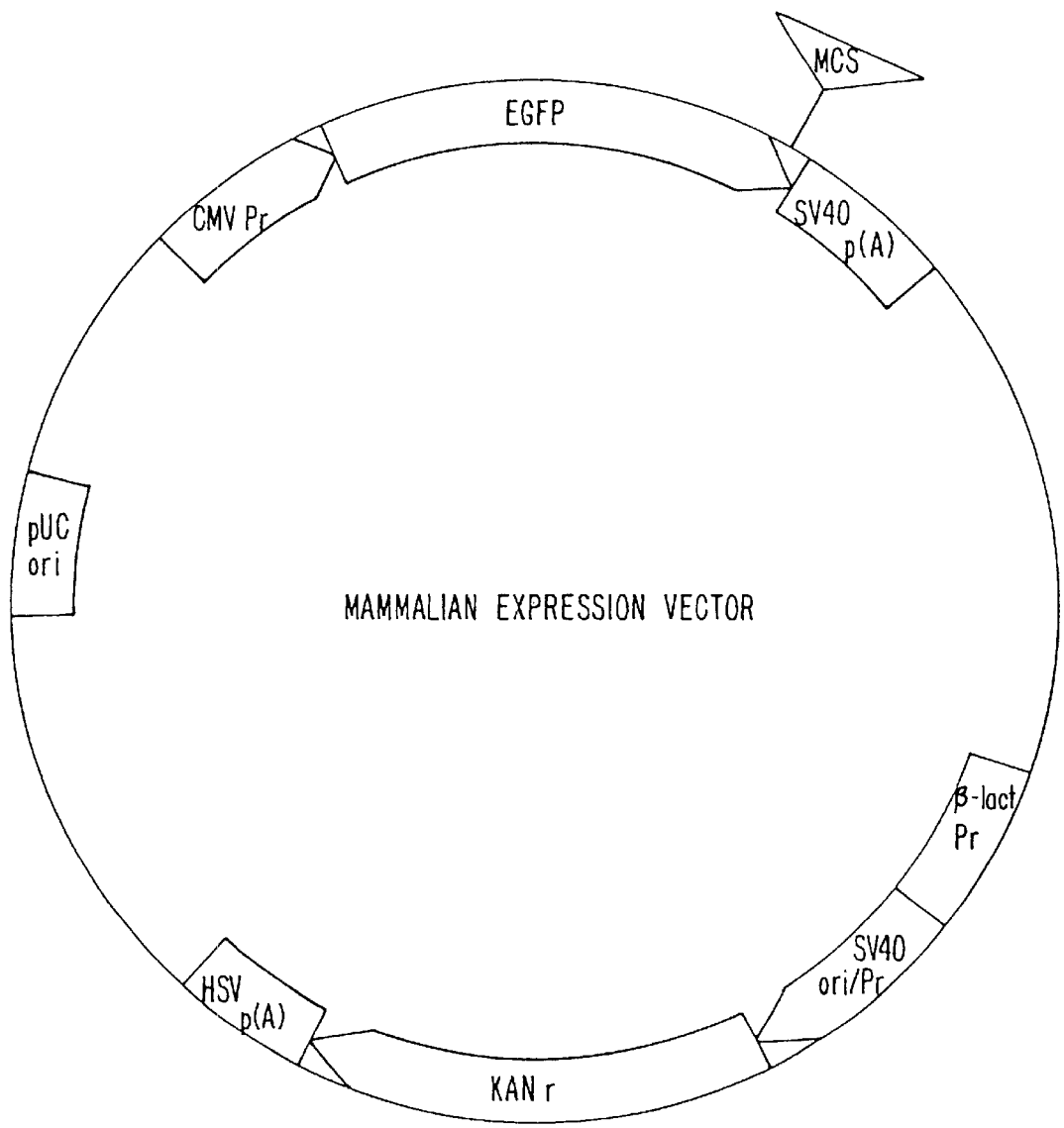
FIG. 2: Mammalian perturbagen expression vectors that use autofluorescent proteins (GFP or BFP) as fusion partners for the expressed proteins. MCS is a multiple cloning site for insertion of individual sequences or genetic libraries. Either of the illustrated vectors may be used for perturbagen expression library construction.
Figure 2:
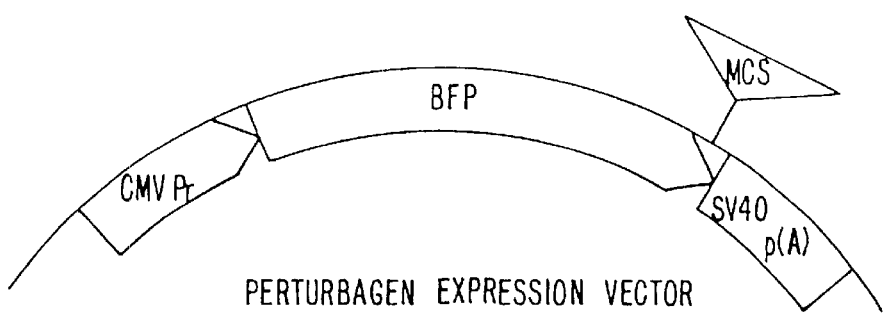

Expression vectors are used in the invention to produce RNA, proteins, protein fragments, or peptides derived from sequences (genes and gene fragments) that are introduced into host cells. The sequences include reporter genes used as a surrogate for the phenotypic state of the cell, and sequences that encode the perturbagens. There are numerous expression vectors known in the art which are readily available for use in the present invention (Ausubel F. M., Brent R., et al., 1996; Sambrook J. et al., 1989). Some of these are tailored for use in specific cell types, but most are designed to be used in a wide variety of cell types. In mammalian cells, viral transcriptional regulatory elements are a typical choice for driving expression of exogenous genes. For the purposes of the present invention involving perturbagen expression in mammalian host cells, an expression vector that contains a reporter gene flanked downstream by a poly(A) addition sequence, e.g., derived from the SV40 TAg gene, may be used. This type of expression vector is illustrated in FIG. 2. The perturbagen-encoding sequence may be flanked upstream of its initiation codon by a TATA box, capable of binding RNA polymerase II (Pol II), and by an enhancer that preferably confers high expression on the linked perturbagen-encoding sequences. In addition to cis regulatory sequences that are constitutively active such as those in powerful viral promoters, the expression vector preferably includes a site appropriate for insertion of perturbagen-encoding library sequences. Such library sequences preferably involve generation of a fusion protein with, e.g., BFP, though native protein domains or protein fragments may also be employed. The choice of which, if any, perturbagen fusion partner to use depends on, e.g., if cytoplasmic, nuclear, or extracellular expression of the perturbagen is desired. The vector, if it is of viral origin, may not require propagation in a bacterial host. However, more typically the vector requires propagation in, e.g., *E. coli,* and contains sequences necessary for replication and selection in *E. coli* such as a colE1 replicon and an antibiotic resistance gene.

For prokaryotic and archaebacterial host cells, cis regulatory sequences are chosen according to similar criteria as discussed above. For the perturbagen expression vector, cis regulatory sequences are included upstream of the perturbagen-encoding sequences that cause robust, preferably high expression levels. These sequences are thus, preferably, of a generic type present, e.g., upstream of housekeeping genes. In *E. coli* for example, a suitable sequence is the consensus promoter that consists of a −10 box and a −35 box (Alberts B., Bray D., et al., 1989; Lewin B., 1994).

Figure 3:
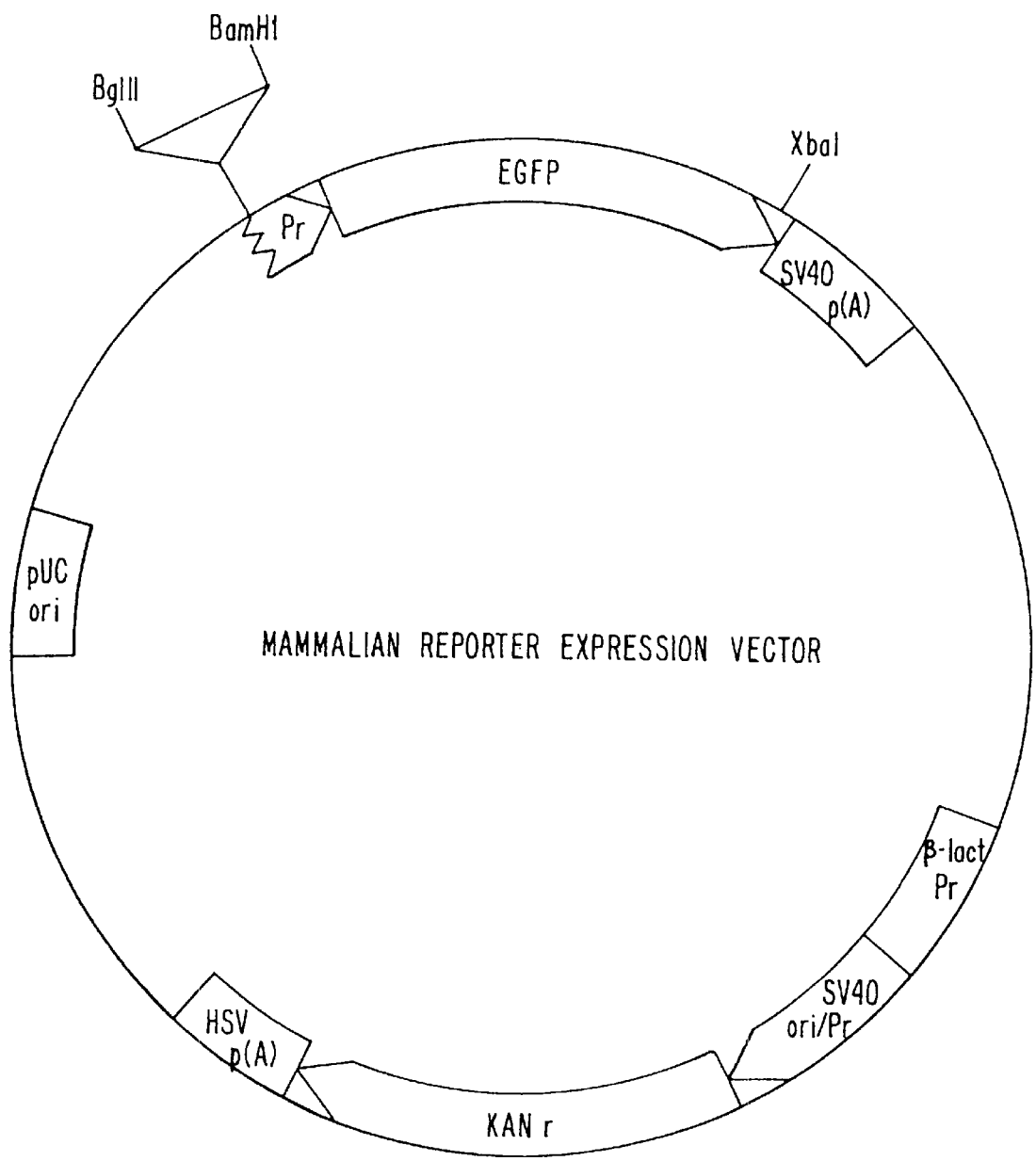
FIG. 3: Reporter gene expression vector for mammalian cells with a "crippled" promoter that contains only the TATA box from the CMV promoter and lacks an enhancer; cis regulatory elements can be inserted upstream of the TATA box in the BglII or BamHI sites.

In contrast to the perturbagen expression vector, the reporter vector is customized so that reporter expression reflects as closely as possible the phenotypic state of the host cell under study. Thus, the expression vector is designed such that the reporter gene (e.g., GFP) is placed under the control of cis regulatory sequences that confer cell-type specific expression, and/or reflect the activation of specific biochemical pathways within the cell. For example, FIG. 3 shows a mammalian expression vector that can be used to insert foreign cis regulatory sequences upstream of the TATA box from the CMV promoter, generating GFP expression under the control of the chosen regulatory element. Such regulatory sequences are known in the art (Lewin B., 1994 and see supra), or they can be identified using methods disclosed in the co-pending United States Patent Application by Carl Alexander Kamb filed Feb. 14, 1997 titled, "Methods for identifying, characterizing, and evolving cell-type specific cis regulatory elements," Attorney Docket No. 20410–701.

Enrichment for Phenocopy Variants Induced by Perturbagen Expression

The combination of genetic libraries and genetic selection or screening techniques permits identification of specific sequences from libraries based on their functions in living cells. This strategy has been used frequently in molecular biology to clone genes based on expression, e.g., by complementation of a mutant phenotype (e.g., Yocum R. R. and Johnston M., *Gene* 32: 75–82 (1984)). The premise of the strategy is that an appropriately constructed library can be introduced into suitable host cells and the effects of the library sequences can be monitored. For example, a particular host cell may die in a particular environment in the absence of a certain gene; the host cell will only grow when a library insert that includes the gene is present. Alternatively, screens can be employed to pick out the library sequences that confer a particular phenotype. For example, the T8 (Leu-2) gene was isolated by a protocol that involved expression in cultured cells, labeling by a fluorescent antibody, and enrichment by FACS of T8-expressing cells (Kavanthes P., Sukhatme V. P., et al., *Proc. Natl. Acad. Sci. (USA)* 81: 7688–7692 (1984)).

Figure 4:
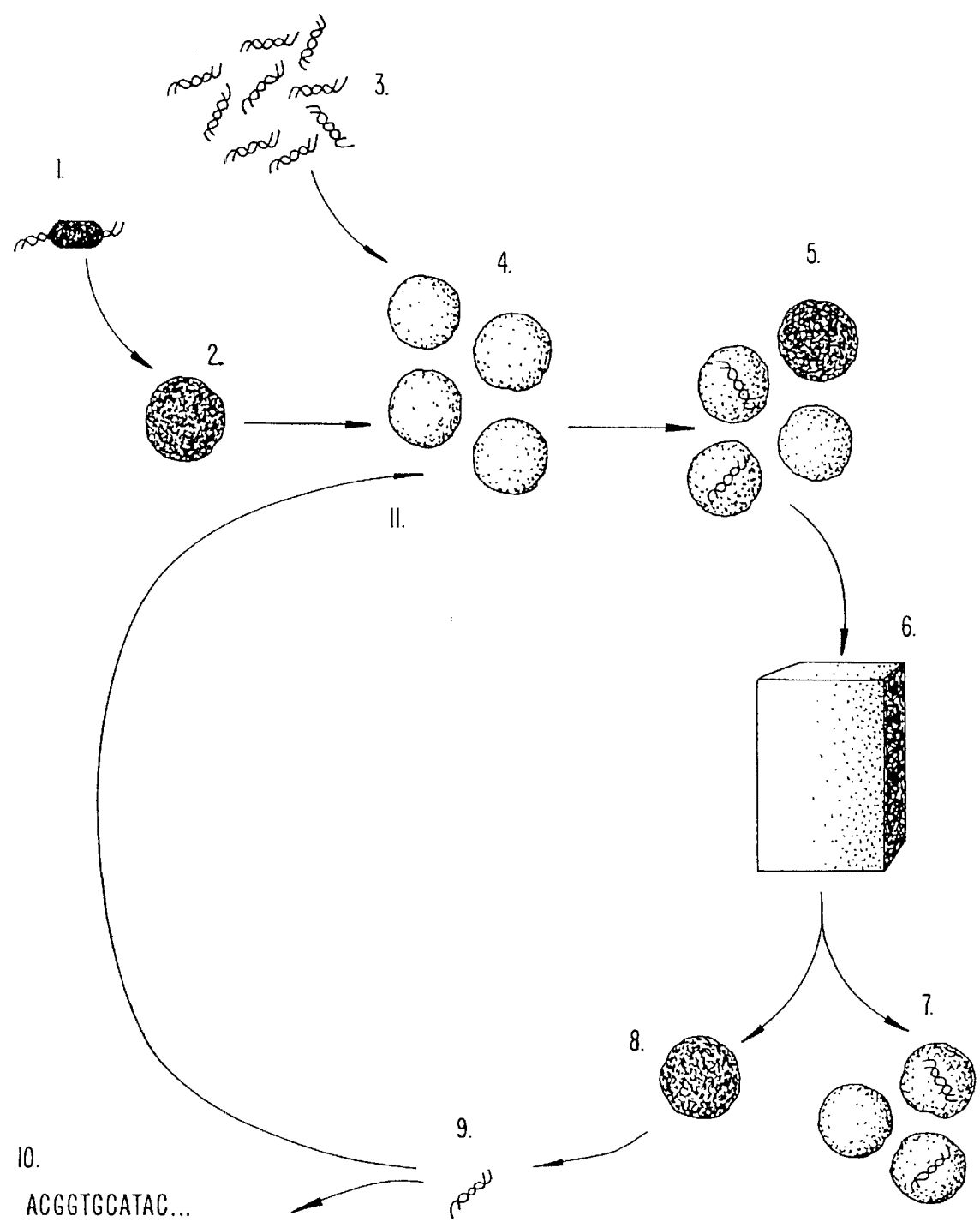
FIG. 4: Flow chart of the process of genetic analysis disclosed in the invention. The reporter expression construct (in this case, the GFP gene) (1) is introduced into the chosen host cells and a stable expresser is selected (2). This reporter-expressing line is clonally expanded to generate a population that is, in this case, bright green (4). A perturbagen library (3) is introduced into the host cells to generate a population of reporter gene-containing cells (5), many of which also express perturbagens. This population is examined using a flow sorter device (6) and cells are sorted into two populations: cells (7) that continue to express reporter protein levels similar to the cell in #4.; and, cells (8) that express, in this case, reduced levels of the reporter. The perturbagen inserts (9) from such "dim" cells are isolated and either used to determine their DNA sequences (10), or reintroduced into the reporter-containing host cells (11) for another cycle of selection and enrichment.
Figure 5:
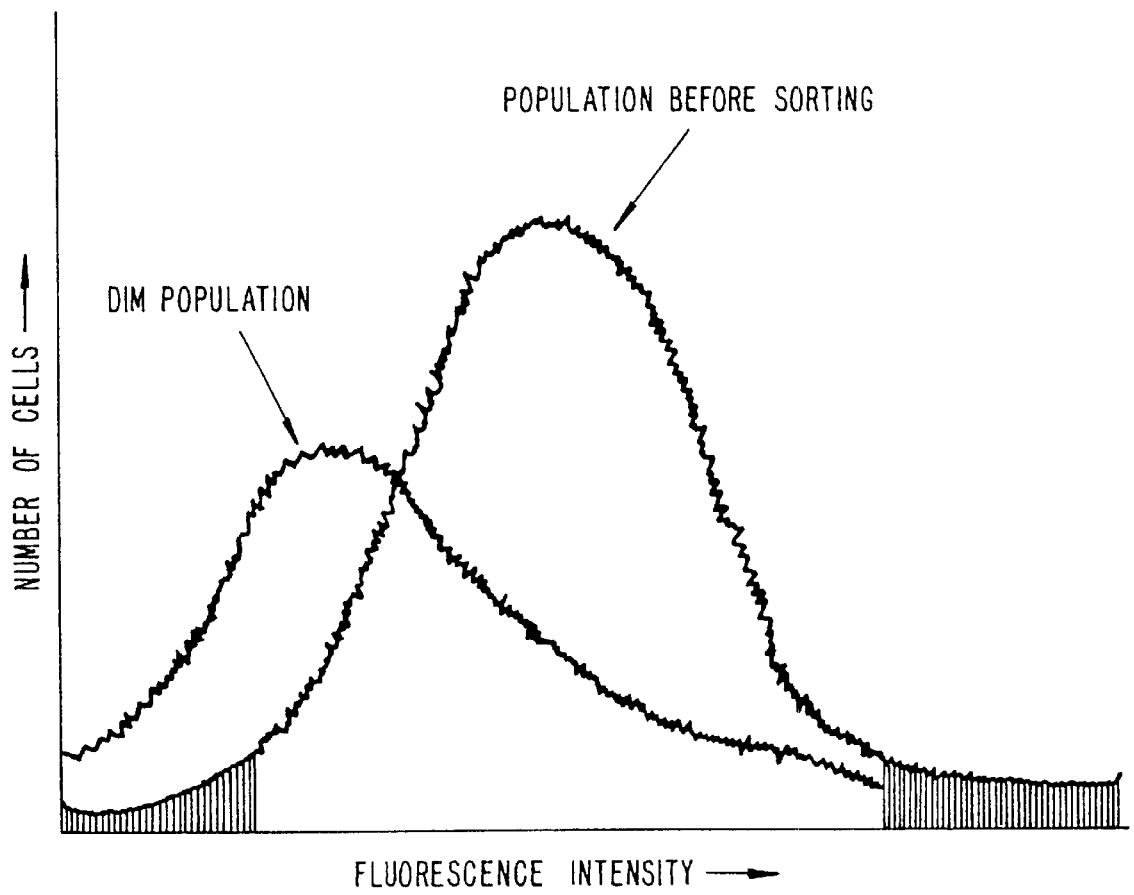
FIG. 5: Flow sorter profile diagram. A cartoon depicting the fluorescence intensity distribution of a population of host cells containing perturbagens prior to selection. This pre-sorted population is used to select cells on the left tail of the distribution (in black fill) or on the right tail (in gray fill). If, for example, the dim cells on the left are selected and perturbagens from these cells are reintroduced into the original host cells, the fluorescence intensity distribution that ensues from cells that harbor such a sub-library of sequences becomes skewed to the left (i.e., the mean fluorescence intensity decreases).

The present invention may use a flow sorter such as a FACS or equivalent device to screen through large numbers of host cells harboring perturbagen library inserts to identify those that have a particular phenotype; namely, cells that have reduced or elevated levels of reporter molecule expression. If the perturbagen library is introduced into host cells engineered to express the reporter (e.g., GFP) in a stable context, the large majority of cells that are analyzed by FACS are expected to have normal (e.g., high) levels of reporter expression. However, a small number may exhibit reduced expression, detected on the FACS as cells that fall on the dimmer side of the cell fluorescence distribution. These dim cells can be collected and grown in isolation of the others. See FIGS. 3 and 4. Such a procedure results in enrichment from the starting population of perturbagen-containing cells for those that contain perturbagens that reduce the level of reporter expression. These selected, dim cells can be used to reisolate the perturbagen fragments by, e.g., PCR using primer sites that flank the library inserts, so as to build a sub-library of perturbagen fragments enriched for those that cause reduced reporter expression. The sub-library of fragments can be recloned (using e.g., the same expression vector) and reintroduced into the host cells, and the screening/selection process can be repeated as many times as necessary.

After a sufficient number of cycles, a substantial difference should be observed in the fluorescence intensity distribution of the original reporter-containing host cells as compared to the host cells harboring the enriched perturbagen sub-library inserts. Preferably, the procedure should be repeated until a minimal overlap is observed between these two fluorescence intensity distributions. Ultimately, the process of FACS sorting and cycling should result in a population of perturbagen fragments that, e.g., inhibit expression of the reporter. These can be isolated and studied individually by molecular cloning and DNA sequence analysis. If a sufficient number of cycles has been carried out, many, preferably most, separate fragments should produce roughly the same effect on reporter expression in the host cells as the effect produced by the enriched population from which they were isolated.

Perturbagen Targets

The targets of perturbagens in cells are as interesting as the perturbagens themselves. It is expected that most perturbagens exert their phenotypic effect on cells by binding another specific protein, thus inhibiting its function. The other protein may be a wild type counterpart of the perturbagen (e.g., in the case of protein homomultimers), or it may be another unrelated protein. In either case, the perturbagen provides a critical probe for isolation of the target protein.

With present technology such as the yeast two-hybrid system or other genetic or biochemical approaches known in the art, it is possible to identify the relevant target molecules in the cell (Fields S. and Song O. -K., U.S. Pat. No. 5,283,173; Serrano M., Hannon G. J., et al., *Nature* 366, 704–707 (1993); Ausubel, et al., 1996). It is also possible that the perturbagen sequence may reveal the probable identity of the target, based on existing knowledge of biochemical pathways and comparisons with sequence databases; for example the sequence of a specific perturbagen can be used to search a public database such as GenBank. Any "hits" that reveal database sequences with homologies that exceed a threshold for statistical significance can be carefully studied, and their biological roles can be investigated in the published literature. In some cases perturbagens will be derived from components of a well established biochemical pathway, and strong candidates for the perturbagens' targets may be deduced from the identity of the perturbagens themselves.

In certain cases, additional perturbagen experiments may reveal the identities of targets. For example, a second perturbagen experiment using cells that express a perturbagen that inhibits reporter gene expression may provide a clue. If cells that harbor the reporter construct plus the initial perturbagen (now expressed stably using methods similar to those employed to generate the original reporter-containing host cells) are used as host cells for another round of perturbagen genetics, it is sometimes possible to select revertants that express high levels of reporter once again. This revertant phenotype may be caused by, among other things, the presence of a second perturbagen in the cells that mimics the behavior of the first perturbagen's target; i.e., a compensatory effect that involves overexpression of the target or a fragment of the target. Thus, the set of revertant perturbagens ("anti-perturbagens") may provide clues as to the nature of perturbagen targets.

Genetic Pathways

The perturbagen approach used in the present invention has the capacity to identify several components of specific genetic pathways in a single selection experiment. This is because the assay is performed using a population of cells, without the need to isolate and grow individual mutants. All cells that harbor perturbagens capable of increasing or decreasing reporter gene expression are collected together, and the family of resident perturbagens can be amplified, e.g., by PCR, for subsequent analysis. Cloning individual nucleic acid fragments is much faster than cloning individual cells and localizing chromosomal mutations within them. In a sense, genetics is performed on the library of perturbagens rather than on the host cells themselves.

Individual perturbagen-encoding fragments can be examined in further detail using assays other than the reporter gene expression assay used for their isolation. The mechanistic basis for perturbagen activity is likely to be of considerable interest. For example, the perturbagen may interfere with reporter gene expression by inhibiting the activity of a transcription factor required for reporter gene expression. Alternatively, it may interfere upstream of the transcription factor in a biochemical pathway that leads to activation of the set of transcription factors required for reporter gene expression. Finally, the perturbagen may cause a transformation in cell fate, such that the host cell no longer resembles the original parental cell type, but instead has been converted into a different cell type. Other possible modes of perturbagen disruption that lead to decreased or increased reporter gene expression can be envisioned. These can be sorted out later using cell biological, genetic, and biochemical methods known in the art (Ausubel, et al., 1994; Sambrook et al., 1989).

During the course of a particular experiment, several perturbagen inserts may be isolated that affect reporter gene expression. Using further rounds of perturbagen selection it is possible to place the perturbagens into groups (akin to classical "complementation groups") based on the step in the pathway that they affect, and even to order those steps. The first stage in this process involves generating a new set of anti-perturbagens that act to increase the reporter expression. If the original reporter gene is constitutively expressed in the absence of perturbagens, for instance, then anti-perturbagens may be selected as bright revertants of dim cells containing a perturbagen isolated during the first round of selection experiments described supra. If the original reporter gene is inducible (see Example 1 infra), it may be simpler to select perturbagens that are bright in the absence of the inducing signal (i.e., they promote constitutive activation). In either case there are now two sets of perturbagens with opposite phenotypes; one class makes cells dim and the other reverses this phenotype. By introducing all possible pairs of "dim-" and "bright-" inducing perturbagens into the host cells and examining the resulting reporter expression levels, it is possible to group perturbagens (and thus their cellular targets) by common response. If it is desirable to order the pathway in detail, methods using conditional perturbagens (hot and cold sensitive) may be employed according to the strategy described by Jarvik J. and Botstein D. (*Proc. Natl. Acad. Sci (USA)*. 70: 2046–2050 (1973); *Proc. Natl. Acad. Sci. (USA)* 72: 2738–2742 (1975)).

Note that perturbagens isolated in the fashion described herein may lead directly to new therapeutic molecules. The goal is not necessarily to identify perturbagens that have a single specific effect on expression of the reporter gene, e.g., by interfering with the function of the reporter itself. Rather, the goal is through this means to identify perturbagens that have more general effects on cell physiology, including but not limited to cell type transformations. Such perturbagens may be relevant to disease therapy because they disrupt specific pathways in cells which have profound phenotypic and physiological consequences. These perturbagens and their associated cellular targets may serve to identify novel therapeutic targets in cells, an extremely valuable commodity in the medical arena.

Additional Manipulations Designed to Improve Perturbagen Specificity

Perturbagens isolated using the procedures described supra may be further refined in two senses. First, perturbagens that are improved variants of members of the original perturbagen library may be isolated by accidental or deliberate mutation or recombination during the process of selection and enrichment. Second, the perturbagens may be passed through additional genetic screens and selections that enrich for those that have more desirable properties in terms of cell-specific activity.

In the first case, amplification of DNA by, e.g., PCR is known to introduce sequence changes during the replication process (Cline J., Braman J. C., et al., *Nucleic Acids Res.* 24, 3546–3551 (1996)). This can lead to sequence variants in subsequent experiments, some of which may have useful properties. For example, they may interfere more effectively with reporter gene expression than the original perturbagen in the library. These perturbagens will be identified by conferring a phenotype of, e.g., even lower reporter expression. Alternatively, it may be desirable to evolve improved variants of existing perturbagens by deliberately subjecting the amplification process to conditions that enhance mutation and/or recombination of the nucleic acid by, e.g., in vitro mutagenesis, error-prone PCR, or recombinational PCR (Stemmer W. P., *Nature* 370, 389–391 (1994)). Such conditions are known in the art (Ausubel et al., 1994) and provide a means for evolving perturbagens that, e.g., are active at lower concentrations and/or demonstrate increased selectivity in cells compared to perturbagens expressed by the original library; thus, they perform better as perturbagens.

In the second case, it may be desirable to passage the sub-library of perturbagen fragments that have been isolated by application of the principles described supra through additional screens to enrich for those with improved selectivity for particular biochemical pathways. For instance, trivial effects on reporter expression, or general effects on gene expression and/or cell viability may be detected or eliminated by appropriate secondary screens. If desired, reporters linked, e.g., to a second tissue- or cell-type-specific promoter that behaves in the host cells in a manner similar to the first reporter gene promoter may be used to reject perturbagens that affect the host cells in a reporter- or promoter-specific manner, and do not have a more profound effect on the state of the cell. Alternatively, a different reporter joined to the first promoter may be used. In addition, perturbagens that have general, non-specific effects on gene expression may be identified and/or removed by passing perturbagen sub-libraries or individual perturbagen-encoding sequences through a different host cell, unrelated to the first host cell, with a different host-cell-specific promoter.

Small Molecule Displacement Screen based on Perturbagen-Target Interactions

Perturbagens isolated as described supra behave in a transdominant mode similar to traditional small molecule pharmaceutical compounds. Thus, in certain cases they may serve much the same function as small molecule therapeutics though it may be necessary to ensure intracellular delivery and expression by gene therapy technology. In addition, perturbagens, in association with their cellular targets, provide the basis for high-throughput in vitro screens for small molecule mimics that have properties similar to the original perturbagen; namely, they bind specifically to the perturbagen target and disrupt the target's function in vivo. Such molecules may have effects on cells similar to the perturbagens used in the screen.

In a specific embodiment of the invention, a system is used for assessing protein-protein interactions and their inhibition in a cell in vivo, e.g., in a bacterial, fungal, plant, insect, or mammalian cell, or in vitro. This system, referred to as a small molecule displacement assay, can be used to screen libraries of small molecules to identify specific compounds that disrupt perturbagen/target interactions. This use of perturbagens and their cognate targets is described in detail in co-pending U.S. patent application of Kamb, C. A. (Docket No. 8835–004-999).

EXAMPLE 1

Figure 6:
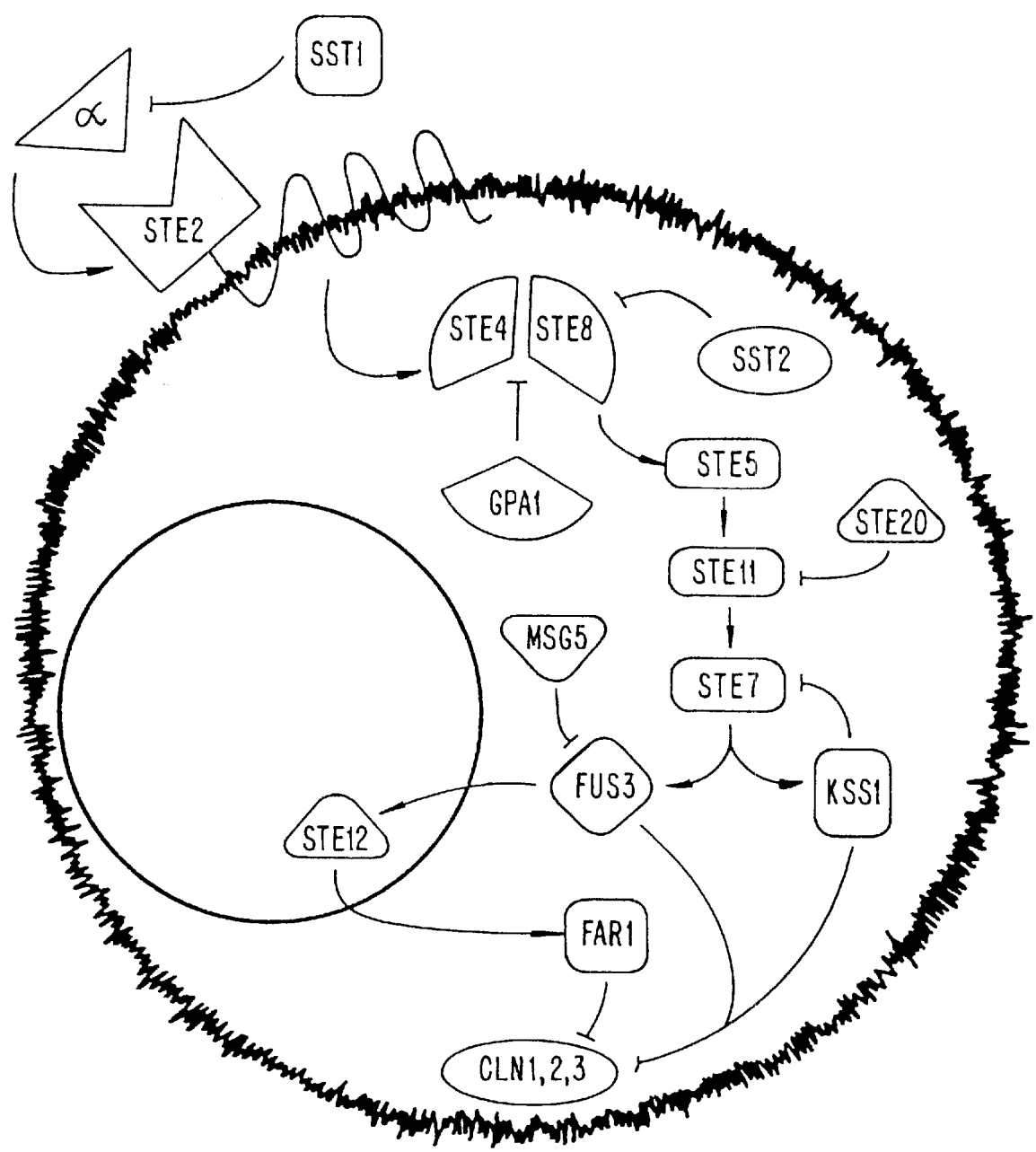
FIG. 6: Genetic pathway involved in a-factor arrest of $S$. cerevisiae $\underline{a}$ cells. The cell and nuclear membranes are represented as gray circles; the protein components of the pathway are depicted as rounded objects of various types including rectangles and triangles. a-factor is the triangle labeled with "a" outside the $\underline{a}$ cell. Interactions among components that lead to activation are represented as arrows; interactions that lead to inhibition are depicted as blunt-ended lines.

Identification of Perturbagens that Modulate the a -Factor Signaling Pathway in Yeast a Cells The binding of yeast mating pheromone a-factor to a specific 7-transmembrane-domain-containing G-protein-coupled receptor (the product of the STE2 gene) on the surface of yeast cells of a mating type activates a signaling pathway that culminates in cell-cycle arrest and the preparation of the cell for mating to an a cell (FIG. 6). This well-characterized signaling pathway (reviewed in Bardwell L., Cook J. G., Inouye C. J., Thorner *J., Dev. Biol.* 166: 2, 363–379 (1994); Herskowitz I., *Cell* 80: 2, 187–197, (1995)) involves activation of a MAP kinase cascade and the transcriptional induction of at least 6 genes. Analysis of the promoters of some of these genes has identified a sequence element that is necessary and sufficient for induction. The method of the invention can be applied to identify perturbagens that block the a-factor signaling pathway and thus prevent the a-factor-dependent induction of specific genes.

Construction of an a-Factor-Responsive GFP Reporter Plasmid

The promoterless yeast plasmid pRS416-GFP (disclosed in the co-pending application by Carl Alexander Kamb filed Feb. 14, 1997 titled, "Methods for identifying, characterizing, and evolving cell-type specific cis regulatory elements") contains the GAL1 TATA box (minus the GAL upstream activation sequences, UAS) upstream of the coding sequence of a GFP variant which expresses well in yeast.

Figure 7:
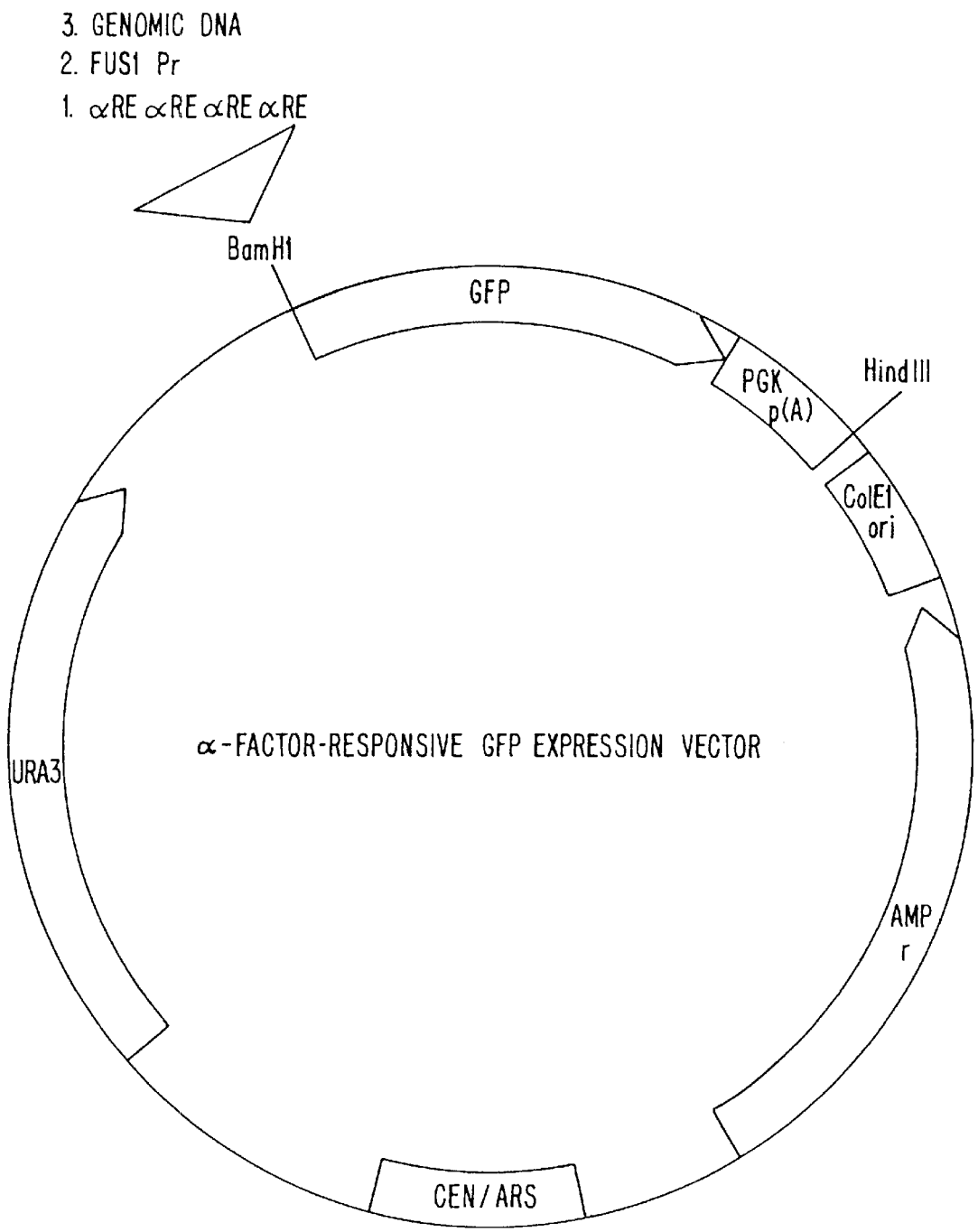
FIG. 7: Expression vector used in yeast as a reporter to identify perturbagens that affect a-factor responsiveness. Three possible inserts upstream of the GFP gene are depicted which depend on the strategy used. The first strategy involves use of four tandemly arrayed a-factor response elements; the second uses the promoter of the FUS1 gene; the third uses genomic DNA selected to confer a-factor responsiveness.

This plasmid can replicate and be selected in yeast (CEN and ARS, URA3) and *E. coli* (ColE1, AmpR) and has a unique BglII site upstream of the GAL1 TATA box for inserting DNA promoter-containing fragments. The GFP expression is rendered a-factor responsive by cloning into the BglII site 4 copies of the a-factor-responsive element (as a synthetic oligo), a PCR fragment containing bases -259 to upstream of the Fus1 gene (Hagen D. C., McCaffrey G., Sprague G. F. Jr., *Mol. Cell Biol.* 11: 6, 2952–61 (1991)) or, alternatively, any other a-factor-responsive cis regulatory element isolated from a genomic library that has been screened to identify such elements according to the methods described in the co-pending United States Patent Application by Carl Alexander Kamb filed Feb. 14, 1997 titled, "Methods for identifying, characterizing, and evolving cell-type specific cis regulatory elements," (Attorney Docket Number 20410–701) (see FIG. 7). When this construct is introduced into yeast and the cells are exposed to a-factor, they show increased fluorescence either by microscopy or FACS analysis compared to the same cells grown in the absence of a-factor. Thus this construct satisfies the conditions necessary for a reporter that can be employed in the invention disclosed herein; namely, the reporter responds in a manner that reflects the relevant phenotypic state of the cell and/or cell environment.

As an alternative to carrying the reporter gene on a centromere-containing plasmid in yeast, the construct can be introduced into the yeast genome using techniques known in the art (Ausubel et al., 1996; Rothstein R. J., *Methods Enzymol.* 101: 202–211, (1983)). Briefly, endogenous pathways of homologous recombination are used in vivo to insert an expression vector that lacks an ARS/CEN but contains a selectable marker in addition to the reporter expression cassette. A region of yeast DNA homology is introduced into the vector and the vector is cut with a restriction enzyme that produces a linear molecule, the ends of which contain homology with a yeast chromosomal region. Transformation with this linear material results in recruitment of homologous recombination machinery and generates a large number of transformants that contain the expression vector inserted into the chromosomal region of homology. Such an expression vector is inherited stably along with the chromosome within which it resides. Individual transformants can be tested to ensure that they continue to express the reporter as they were intended.

Construction of a Yeast Genomic DNA Perturbagen Library

Standard techniques are used to construct a library of yeast genomic DNA fragments in a yeast/*E. coli* shuttle vector such as pRS315 (Sikorski R. S., Hieter P., *Genetics* 122: 1, 19–27 (1989)). This vector contains LEU2 as a selectable marker in yeast. Four separate libraries may be made to present the perturbagen in different contexts or cellular compartments. In all four cases there is a GAL1 promoter upstream of the inserted genomic fragment in order to drive its expression in a galactose-dependent fashion.

Figure 8:
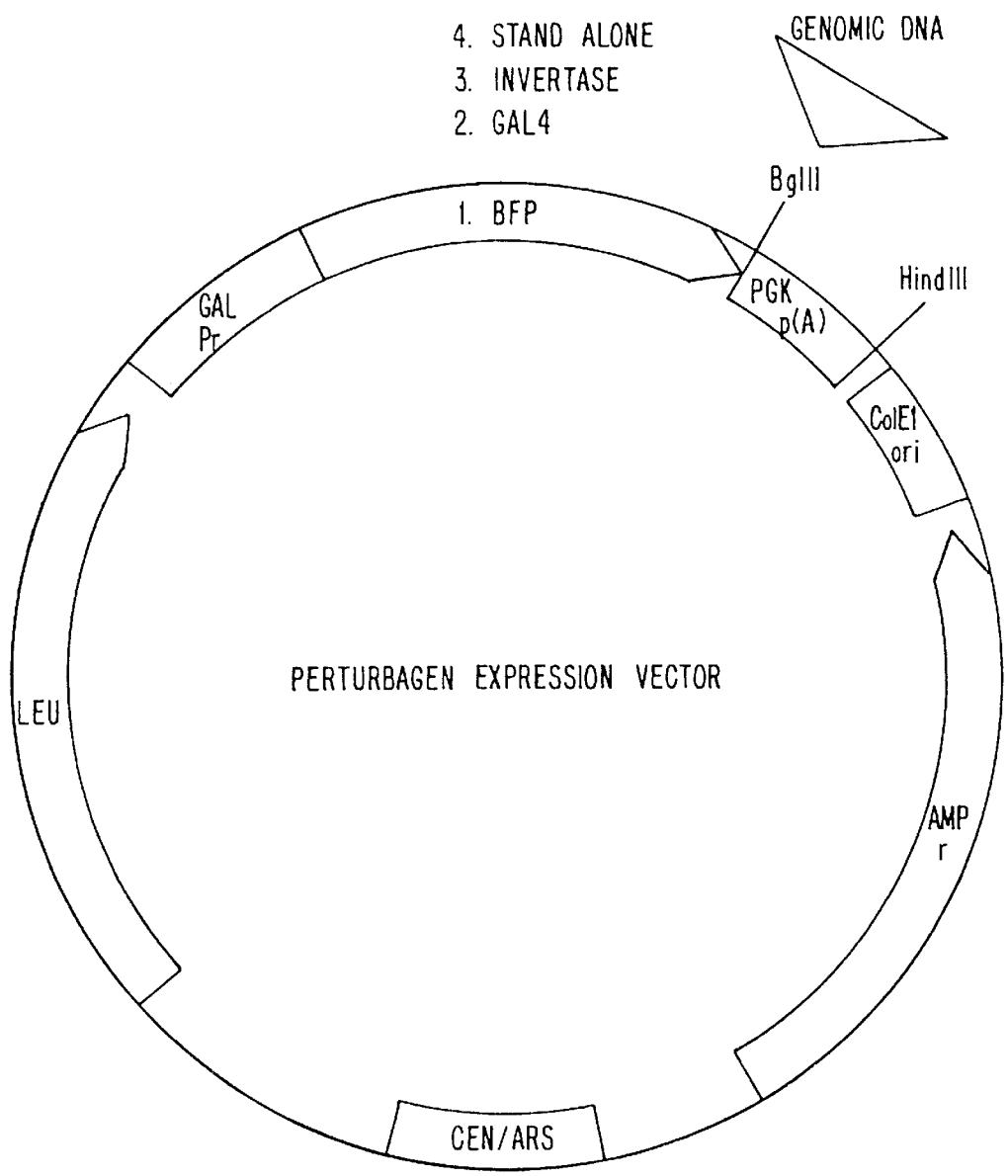
FIG. 8: Expression vector to express perturbagens in yeast. "Genomic DNA" refers to the perturbagen-encoding inserts. Four strategies are used to generate fusion proteins with the perturbagen inserts: 1. Blue Fluorescent Protein (BFP); 2. GAL4 sequences; 3. invertase sequences; 4. no fusion partner sequence.

In one vector the coding sequence for Blue Fluorescent Protein (BFP) (Quantum Biotechnologies, Inc., Laval, Canada; Anderson M. T., Tjioe I. M., Lorincz M. C., Parks D. R., Herzenberg L. A., Nolan G. P., Herzenberg L. A., *Proc. Natl. Acad. Sci.* (*USA*) 93: 16, 8508–8511 (1996)) is located downstream of the GAL promoter and upstream of the insertion site to allow translational fusions between BFP and the inserted coding sequence (see FIG. 8). In a second case the secreted form of invertase is the fusion partner; this allows export into the secretion pathway of the perturbagens and may provide a mechanism for isolating perturbagens that have activity when secreted outside the cell or when otherwise consigned to the secretory pathway. In a third case the GAL4 protein, a well established fusion partner (Fields S. and Song O. -K., U.S. Pat. No. 5,283,173), is fused to the perturbagen; this facilitates import of the perturbagen into the nucleus. In a fourth case there is no fusion partner for the perturbagen sequence; this allows production of "stand alone" perturbagens.

Analysis of the Library in (a-Factor-Responsive) GFP Reporter-Bearing a Cells

Each of the perturbagen libraries described above is introduced into separate cell populations containing the a-factor-responsive GFP vector. The selectable markers used on the perturbagen and reporter plasmids are different so that both can be maintained in the same cell (e.g., URA3 and LEU2). Alternatively the reporter construct can be integrated into the chromosome (which has advantages due to more uniform levels of reporter gene expression in the population of cells).

A perturbagen that specifically blocks the a-factor signaling pathway should reduce fluorescence of these cells in a galactose-dependent fashion. The perturbagen sub-library can be further tested to ensure that, e.g., expression of particular perturbagens does not simply kill cells. This manipulation provides a convenient counterscreen to increase the probability that the perturbagens are specific for the targeted biochemical pathway involving α-factor arrest.

It is also possible to reverse the selection process and identify perturbagens that have the opposite effect; namely, they increase reporter expression in the absence of a-factor and the presence of galactose. Such perturbagens may be isolated by screening for perturbagen-containing cells that are bright in the presence of galactose and the absence of a-factor.

Note that it is possible to use the BFP perturbagen library in this sort (the second case above) because levels of GFP expression in a cell can be monitored independently of the BFP expression in the same cell by the appropriate use of bandpass filters in the FACS machine. Because the excitation and emission maxima of GFP differ from those of BFP, it is necessary to employ appropriate filters and lasers (Anderson, et al., 1996).

EXAMPLE 2

Pathway that Leads to Expression of the Tyrosinase Gene in Melanoma Cells

A variety of human melanoma-specific genes have been identified including DOPAchrome tautomerase/tyrosinase-related protein 2 (TRP-2) (Yokoyama K., Yasumoto K., et al., *J Biol. Chem.* 269: 27080–27087 (1994)), melanotransferrin (Mtf) (Duchange N., Ochoa A., et al., *Nucleic Acids Res.* 20: 2853–2859 (1992)), microphthalmia-associated transcription factor (MITF) (Fuse N., Yasumoto K., et al., *Biochem. Biophys. Res. Commun.* 219: 702–707 (1996), and tyrosinase (Shibata K., Muraosa Y., et al, *J Biol. Chem.* 267: 20584–20588 (1992)). The associated regulatory elements of these genes provide the basis for designing melanoma cell-specific reporters that involve fusion of a reporter gene to the cis regulatory sequences of a melanoma-specific gene.

Construction of a GFP Expression Vector with Tyrosinase Regulatory Elements

Tyrosinase encodes an enzyme involved in the conversion of tyrosine into the polymeric, light-absorbing pigment melanin. Regulatory sequences in the human tyrosinase gene are particularly well characterized. Transfection experiments have determined that a promoter fragment located between 1.8–2.7 kilobase pairs upstream of the tyrosinase transcriptional initiation site is sufficient to confer expression specifically in melanoma pigment-producing cells (Shibata K., Muraosa Y., et al., 1992). Further deletion analysis identified a pigment-cell specific enhancer contained on a 200 base pair fragment located 1.8–2.0 kilobase pairs upstream of the start site. A 39-base pair core element was sufficient to confer melanoma cell-specific expression.

The promoter region defined in the series of experiments described supra is used to direct expression of a reporter gene (GFP in this case) specifically in human melanoma cells. Numerous such cultured cell lines are available (Satyamoorthy K., DeJesus E., et al., Melanoma Res. (In press)), many of which (e.g., HS294T) grow well in culture and can be used in the experiments described in this example. The promoter region may include the entire 2.7 kilobase pairs upstream of the human tyrosinase gene, or the 200 base pair fragment located upstream of a TATA box sequence (FIG. 3). Based on the published literature, such a construct should be selectively active in melanoma cells and not in, e.g., fibroblast cells.

The fusion construct consisting of tyrosinase regulatory sequences joined to the GFP reporter will be introduced in an expression vector such that GFP is expressed at high levels in the host cells. Selection for stable expressers will be applied using, e.g., the dominantly selectable marker for neomycin resistance carried on the expression vector such as that shown in FIG. 3. Stable expressers will be selected using techniques known in the art (Ausubel et al., 1996), and the population of GFP-expressing cells will be verified by flow cytometry. A suitable clone, characterized by high, stable expression of GFP will be employed in subsequent experiments.

Screen for Perturbagens that Inhibit Tyrosinase Expression

This host cell line will be used as a recipient for transfer of a perturbagen library of the type described supra. Briefly, the library consists of cDNA fragments (derived from, e.g., randomly primed human fetal brain mRNA) or random peptide-encoding sequences carried on an expression vector that, e.g., may be derived from a typical mammalian expression vector such as that shown in FIG. 2. In this case, the library is under control of CMV sequences. The library is introduced into the host cells using standard protocols for electroporation (Ausubel et al., 1996). The specific conditions are chosen to optimize nucleic acid transfer (see Example 3). The cells are then passed through a flow sorter device such as a FACS to collect cells that are dim (i.e., express levels of GFP that are lower than the mean level of GFP expression in the host cells that lack perturbagens, or are lower than the mean level of GFP expression exhibited by the bulk population of host cells, many of which express perturbagens). The resident perturbagen-encoding DNA inserts contained within the dim cells are recovered by, e.g., PCR amplification using primer sites that flank the perturbagen insert sequences. These perturbagen fragments are recloned in the expression vector and the sub-library is reintroduced into the reporter-bearing host cells. This cycling process is continued a sufficient number of times to generate a reasonably pure set of perturbagen fragments that have the effect, when introduced singly into host cells, of depressing GFP expression. Such fragments can be characterized further, including determination of their DNA sequences and examination of their effects on the gross phenotype of the cell.

EXAMPLE 3

Pathway that Leads to Expression of Beta-3 Integrin in Metastatic Melanoma

A common feature of advanced melanomas is high level expression of the adhesion molecule beta-3 integrin (Vamer J. A. and Cheresh D. A., Curr. Opin. Cell Biol. 8: 724–730 (1996)). This provides an example of how the invention disclosed herein can be used to identify perturbagens (and perturbagen targets) involved in the expression of specific cell surface molecules.

Transfer of Perturbagen Libraries into Melanoma Cells

Melanoma cells that over express beta-3 integrin are used as the departure point for these experiments. When stained with a monoclonal antibody that binds beta-3 integrin, these cells reveal a reproducible high level of expression that is quantitatively distinct from a variety of other cell types that express either low levels of beta-3 integrin, or none at al, e.g., normal melanocytes. The cell line chosen from among the set of high beta-3-integrin-expressing lines described in Satyamoorthy K., DeJesus E., et al., *Melanoma Res.* (in press) is first tested to optimize nucleic acid transfer using, e.g., electroporation. Standard GFP expression vectors such as those sold by Clontech (Palo Alto, Calif.) provide a convenient method to assess the results of different electroporation conditions. The GFP expression vectors are introduced into the cells using a variety of voltages and capacitances and the cells are returned to culture for a period (typically one day) sufficient to permit recovery of the cells and expression of the transferred DNA. The cells are then analyzed by a flow sorter such as a FACS to determine the percentage of cells that are bright; i.e., the fraction that have accepted the transferred DNA. Conditions are selected that maximize this number for further experiments.

Flow Sorter Analysis and Selection of Dim Cells

A perturbagen expression library of the type described in Example 2 is introduced into the melanoma host cells using the conditions defined above. After one to three days, the cells are collected, stained with the monoclonal antibody directed against beta-3 integrin, and labeled with a secondary fluorescently-labeled antibody that allows indirect visualization of the beta-3 integrin on the cells by binding the Fc domain of the first antibody (Robinson J. P., Darzynkiewicz Z., et al., (Eds.), *Current Protocols in Flow Cytometry,* John Wiley and Sons, New York (1997); Ausubel et al., 1996). These stained cells are passed through a flow sorter, e.g., a FACS, and the dim fraction of cells is collected. The collected cells are lysed and their perturbagen inserts are recovered by PCR for either another cycle of enrichment or for sequence analysis. In either case the inserts are recloned in *E. coli* before proceeding. Individual perturbagen fragments identified through the above procedure are analyzed further to ensure that many (preferably the majority) have the expected properties when tested singly, as opposed to being part of a population. The majority of such fragments, when introduced alone into the melanoma cells, should cause a decrease in the level of beta-3 integrin protein expressed at the cell surface. The DNA sequences of these fragments can be determined and used to explore the public sequence databases to check if they match a known protein. The results of such a search may provide valuable information about the nature of the perturbagen interaction in cells (i.e., the mechanism of the effect) and may point to the perturbagen target in vivo. The perturbagen target may also be found using the method of two-hybrid analysis in *S. cerevisiae* as described in (Fields S. and Song O. -K., U.S. Pat. No. 5,283,173; Serrano et al., 1993).

The above examples are provided to illustrate the invention but not to limit its scope. Other variants of the invention will be readily apparent to one of ordinary skill in the art and encompassed by the appended claims. All publications, patents, and patent applications cited herein are hereby incorporated by reference.

What is claimed is:

1. A method for identifying nucleic acids encoding expression products that alter a phenotype of interest, comprising:
   (a) providing a first plurality of host cells that have a host cell phenotype of interest, each cell comprising a recombinant reporter gene operably linked to a cell-type-specific or cell-state-specific cis regulatory sequence that interacts with a polypeptide encoded on a host cell chromosome, wherein the cis regulatory sequence is selected to correlate the level of reporter gene expression to the host cell phenotype if interest and the level of reporter gene expression is a surrogate for the host cell phenotype of interest;
   (b) introducing a perturbagen expression library into the first plurality of host cells;
   (c) selecting from the first plurality of host cells one or more host cells having a reporter gene expression level falling within a desired range; and
   (d) recovering from the selected host cells a sub-library of nucleic acids comprising one or more nucleic acids encoding one or more perturbagens that alter the level of the surrogate reporter gene expression and the correlative host cell phenotype of interest.

2. The method of claim 1, wherein the perturbagen expression library comprises inserts with sizes that range from approximately 10 base pairs to approximately 10,000 base pairs.

3. The method of claim 1, wherein the selecting step comprises the use of a flow sorter.

4. The method of claim 1, wherein the reporter gene encodes a molecule capable of generating light emission that is detectable above background light generated by host cell molecules other than the reporter.

5. The method of claim 1, wherein the reporter gene encodes a molecule capable of fluorescing and wherein the fluorescence is detectable above background fluorescence emitted by host cell molecules other than the reporter.

6. The method of claim 1, wherein the reporter gene encodes a molecule that inserts into the host cell membrane.

7. The method of claim 1, wherein the reporter gene encodes an intracellular molecule.

8. The method of claim 1, wherein the perturbagen expression library comprises a selectable marker sequence.

9. The method of claim 8, wherein the selectable marker sequence confers antibiotic resistance to the host cells.

10. The method of claim 1, wherein the host cells are bacteria.

11. The method of claim 1, wherein the host cells are archaebacteria.

12. The method of claim 1, wherein the host cells are fungi.

13. The method of claim 1, wherein the host cells are from a plant.

14. The method of claim 1, wherein the host cells are from an insect.

15. The method of claim 1, wherein the host cells are from a mammal.

16. The method of claim 1, wherein the perturbagen expression library comprises sequences encoding fusion products between the coding sequences in the library inserts and a nucleic acid sequence encoding an amino acid sequence with predetermined characteristics.

17. The method of claim 16, wherein the amino acid sequence with predetermined characteristics comprises a second reporter molecule.

18. The method of claim 16, wherein the amino acid sequence with predetermined characteristics promotes export of the fusion product out of the host cell or into the host cell secretory pathway.

19. The method of claim 16, wherein the amino acid sequence with predetermined characteristics promotes import of the fusion product into the nucleus of the host cell.

20. The method of claim 16 wherein said fusion products present said library inserts as insertion sequences within said nucleic acid sequence encoding an amino acid sequence with predetermined characteristics.

21. The method of claim 1 further comprising expressing in the host cells prior to the introducing step (b) a first nucleic acid encoding an expression product that affects the level of reporter gene expression, and recovering in step (d) one or more nucleic acids encoding perturbagen expression products capable of at least partially enhancing the effects of the first nucleic acid on the level of reporter gene expression and the correlative phenotype of interest in the host cells.

22. The method of claim 1 further comprising expressing in the host cells prior to the introducing step (b) a first nucleic acid encoding an expression product that affects the level or reporter gene expression, and recovering in step (d) one or more nucleic acids encoding perturbagen expression products capable of at least partially enhancing the effects of the first nucleic acid on the level or reporter gene expression and the correlative phenotype or interest in the host cells.

23. The method of claim 1 wherein said perturbagen expression products are proteinaceous.

* * * * *

SEQUENCE LISTING

<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: Hypothetical sequence for illustrative purposes

<400> SEQUENCE: 1
acggtgcata c                                                          11